United States Patent
Okamoto et al.

(10) Patent No.: US 9,542,762 B2
(45) Date of Patent: Jan. 10, 2017

(54) X-RAY CT APPARATUS AND IMAGE RECONSTRUCTION METHOD

(71) Applicant: HITACHI, LTD., Tokyo (JP)

(72) Inventors: Shuichi Okamoto, Tokyo (JP); Hiroto Kokubun, Tokyo (JP); Fuyuhiko Teramoto, Tokyo (JP)

(73) Assignee: HITACHI, LTD., Tokyo (JP)

(*) Notice: Subject to any disclaimer, the term of this patent is extended or adjusted under 35 U.S.C. 154(b) by 0 days.

(21) Appl. No.: 14/763,329

(22) PCT Filed: Feb. 18, 2014

(86) PCT No.: PCT/JP2014/053677
§ 371 (c)(1),
(2) Date: Jul. 24, 2015

(87) PCT Pub. No.: WO2014/129428
PCT Pub. Date: Aug. 28, 2014

(65) Prior Publication Data
US 2015/0356756 A1 Dec. 10, 2015

(30) Foreign Application Priority Data
Feb. 21, 2013 (JP) .................................. 2013-032438

(51) Int. Cl.
*A61B 6/00* (2006.01)
*G06T 11/00* (2006.01)
(Continued)

(52) U.S. Cl.
CPC ............. *G06T 11/005* (2013.01); *A61B 6/032* (2013.01); *A61B 6/5264* (2013.01); *G06T 7/0012* (2013.01); *G06T 2207/10081* (2013.01)

(58) Field of Classification Search
CPC ..... A61B 6/032; A61B 6/5264; G06T 7/0012; G06T 11/005; G06T 2207/10081
See application file for complete search history.

(56) References Cited

U.S. PATENT DOCUMENTS 6,894,494 B2 * 5/2005 Stergiopoulos .... G01R 33/5673
324/309
6,934,357 B2 * 8/2005 Boyd ..................... A61B 6/032
378/62
(Continued)

FOREIGN PATENT DOCUMENTS

JP 2011-50509 3/2011
JP 2011-125700 6/2011
(Continued)

OTHER PUBLICATIONS

Isola et al., "Cardiac motion-corrected iterative cone-beam CT reconstruction using a semi-automatic minimum cost path-based coronary centerline extraction", 2012, Computerized Medical Imaging and Graphics vol. 36, 215-226.*
(Continued)

*Primary Examiner* — Katrina Fujita
(74) *Attorney, Agent, or Firm* — Cooper & Dunham LLP

(57) ABSTRACT

To provide an X-ray CT apparatus and an image reconstruction method that can generate an image in which motion influence of a site to be scanned is reduced, the image processing device 403 of the X-ray CT apparatus 1 calculates a reconstruction data range which is a range of projection data to be used for reconstruction based on a motion direction of the site to be scanned. An image is reconstructed using the projection data in the calculated reconstruction data range. The reconstruction data range is set as the projection data in a projection range of at least 180 degrees or more including a projection direction that approximately corresponding to the motion direction of the site to be scanned.

16 Claims, 26 Drawing Sheets

(51) Int. Cl.
*G06T 7/00* (2006.01)
*A61B 6/03* (2006.01)

(56) References Cited

U.S. PATENT DOCUMENTS

| | | | | |
|---|---|---|---|---|
| 7,494,277 | B2* | 2/2009 | Setala | A61B 6/08 378/163 |
| 7,558,439 | B2* | 7/2009 | Weese | G06T 5/50 382/294 |
| 7,787,927 | B2* | 8/2010 | Wood | A61B 6/032 378/20 |
| 8,437,524 | B2* | 5/2013 | Bontus | A61B 6/032 382/131 |
| 8,600,132 | B2* | 12/2013 | Razifar | A61B 6/032 382/128 |
| 8,761,478 | B2* | 6/2014 | Hsieh | A61B 6/032 378/4 |
| 8,923,590 | B2* | 12/2014 | Chen | G06T 7/0083 382/131 |
| 9,060,733 | B2* | 6/2015 | Bruder | A61B 6/032 |
| 9,117,289 | B2* | 8/2015 | Matsumoto | A61B 6/50 |
| 2010/0111393 | A1* | 5/2010 | Okumura | A61B 6/032 382/131 |
| 2011/0052027 | A1 | 3/2011 | Noshi et al. | |
| 2011/0142314 | A1 | 6/2011 | Hsieh et al. | |
| 2011/0293155 | A1 | 12/2011 | Nakanishi et al. | |
| 2012/0207355 | A1* | 8/2012 | Kokubun | A61B 6/503 382/103 |
| 2013/0182935 | A1* | 7/2013 | Wang | G06T 7/2033 382/133 |

FOREIGN PATENT DOCUMENTS

| | | |
|---|---|---|
| JP | 2011-245281 | 12/2011 |
| JP | 2012-19892 | 2/2012 |

OTHER PUBLICATIONS

Rit et al., "On-the-fly motion-compensated cone-beam CT using an a priori model of the respiratory motion", 2009, Medical Physics vol. 36, 2283-2296.*
Schirra et al., "Improvement of cardiac CT reconstruction using local motion vector fields", 2009, Computerized Medical Imaging and Graphics vol. 33, 122-130.*
van Stevendaal et al., "A motion-compensated scheme for helical cone-beam reconstruction in cardiac CT angiography", 2008, Medical Physics vol. 35, 3239-3251.*
Ehrhardt et al., "An optical flow based method for improved reconstruction of 4D CT data sets acquired during free breathing", 2007, Medical Physics vol. 34, 711-720.*
Glover et al., "Projection Reconstruction Techniques for Reduction of Motion Effects in MRI", 1992, Magnetic Resonance in Medicine vol. 28, 275-289.*
Guckenberger et al., "Is a single respiratory correlated 4D-CT study sufficient for evaluation of breathing motion?", 2007, Int. J. Radiation Oncology Biol. Phys., vol. 67, No. 5, 1352-1359.*
International Search Report in PCT/JP2014/053677.

* cited by examiner

FIG. 11
(a)
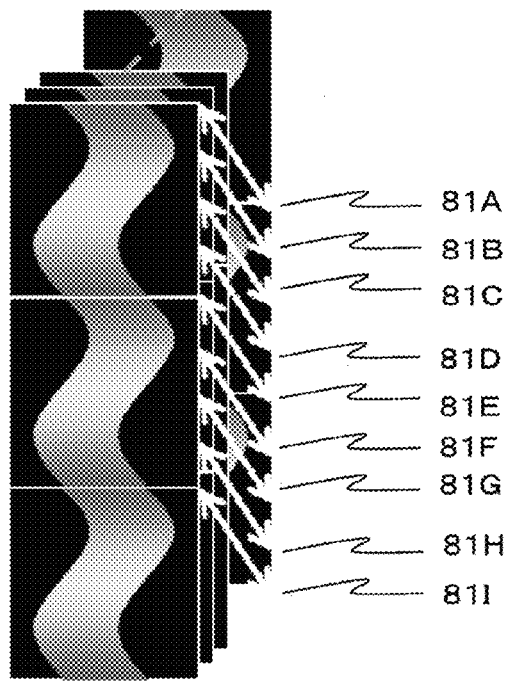
- 81A
- 81B
- 81C
- 81D
- 81E
- 81F
- 81G
- 81H
- 81I
(b)
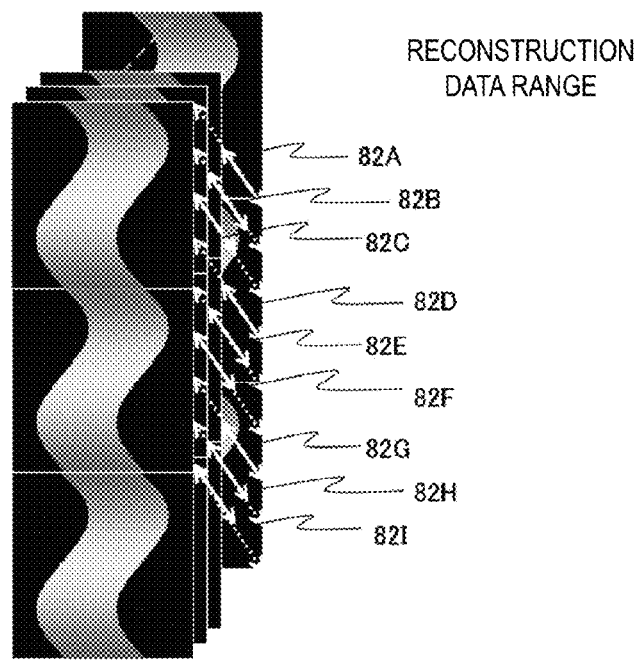
RECONSTRUCTION DATA RANGE
- 82A
- 82B
- 82C
- 82D
- 82E
- 82F
- 82G
- 82H
- 82I 403d MOTION DIRECTION DATABASE

| SITE TO BE SCANNED | POSTURE | MOTION DIRECTION |
|---|---|---|
| THORAX | SUPINE | VERTICAL |
| THORAX | RECUMBENT | HORIZONTAL |
| ⋮ | ⋮ | ⋮ |
| HEART | SUPINE | HORIZONTAL |
| HEART | RECUMBENT | VERTICAL |
| ⋮ | ⋮ | ⋮ |

FIG. 19
(a)
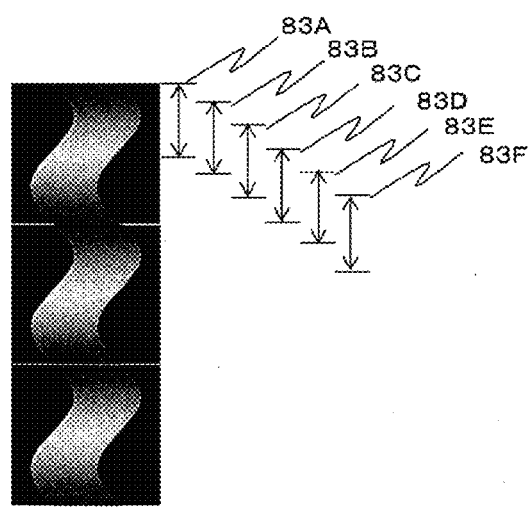
(b)
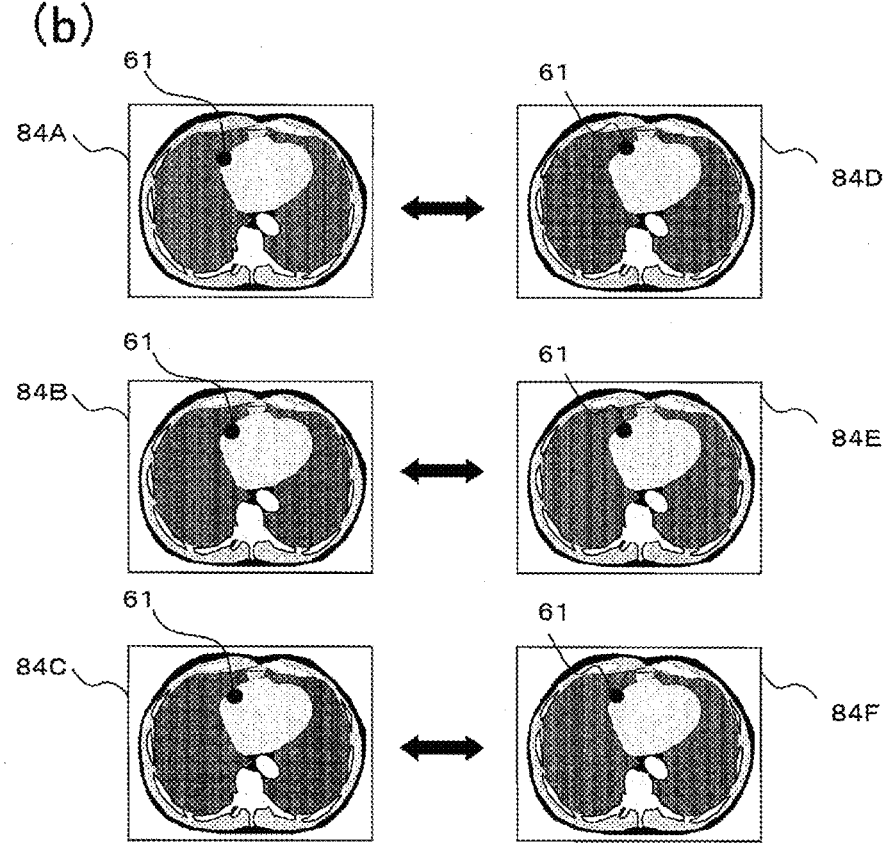

X-RAY CT APPARATUS AND IMAGE RECONSTRUCTION METHOD

TECHNICAL FIELD

The present invention relates to an X-ray CT apparatus and an image reconstruction method suitable for image reconstruction of a moving site.

BACKGROUND ART

When a moving site of the human body is scanned by an X-ray CT (Computed Tomography) apparatus, artifacts caused by motions occur in an acquired image. An X-ray CT apparatus generally scans an object from a plurality of projection angles in a circumferential direction to reconstruct a tomographic image using at least 180 degrees of projection data. Therefore, the above artifacts include at least 180 degrees of motion artifacts.

In order to reduce such motion artifacts, the method in which a motion amount and a motion speed of a site to be scanned are measured using a biosensor such as an electrocardiograph and a respiration sensor, a phase with the minimal motion amount is calculated, and an image is reconstructed by selecting projection data of the calculated phase has been proposed (Patent Literature 1).

CITATION LIST

Non-Patent Literature

PTL 1: Japanese Patent Application Publication No. 4487095

SUMMARY OF INVENTION

Technical Problem

However, even if an image is reconstructed based on a motion amount and a motion speed of a site to be scanned as described above without considering a motion direction, artifacts may become large conversely. For example, in scanning of the heart etc. moving periodically, there is a feature that the motion easily influences projection data scanned in the opposite position to the anteroposterior direction of an object though the motion hardly influences the projection data scanned in the opposite position to the horizontal direction of the object.

The present invention was made in light of the above problems and has a purpose for providing an X-ray CT apparatus and an image reconstruction method that can generate an image in which motion influence of a site to be scanned is reduced

Solution to Problem

In order to achieve the above purpose, the first invention is an X-ray CT apparatus and comprises an X-ray source for irradiating an X-ray to an object from the surroundings; an X-ray detector for detecting an X-ray transmitted through the object; an image processing device for generating projection data from the detected information about the transmitted X-ray and reconstructing a tomographic image of the object based on the projection data; and a display device for displaying the tomographic image, and the image processing device comprises a motion direction obtaining unit for obtaining a motion direction of a site to be scanned; a reconstruction data range calculation unit for calculating a reconstruction data range that is a range of projection data to be used for reconstruction based on the motion direction; and an image reconstruction unit for reconstructing an image using the projection data of the calculated reconstruction data range.

Also, the second invention is an image reconstruction method and includes a projection data generating step of generating projection data that scans the inside of an object; a motion direction obtaining step of obtaining a motion direction of a site to be scanned; a reconstruction data range calculation step of calculating a reconstruction data range that is a range of projection data to be used for reconstruction based on the motion direction; and an image reconstruction step of reconstructing an image using the projection data of the calculated reconstruction data range.

Advantageous Effects of Invention

The present invention can provide an X-ray CT apparatus and an image reconstruction method that can generate an image in which motion influence of a site to be scanned is reduced.

BRIEF DESCRIPTION OF DRAWINGS

FIG. 8 is an example of the motion direction manual setting window 9a.

FIG. 11 is a diagram explaining a reconstruction data range in a volume scan.

FIG. 19 is a diagram explaining motion direction detection based on an image.

DESCRIPTION OF EMBODIMENTS

Hereinafter, referring to the attached diagrams, the suitable embodiments of the present invention will be described in detail.

Figure 1:
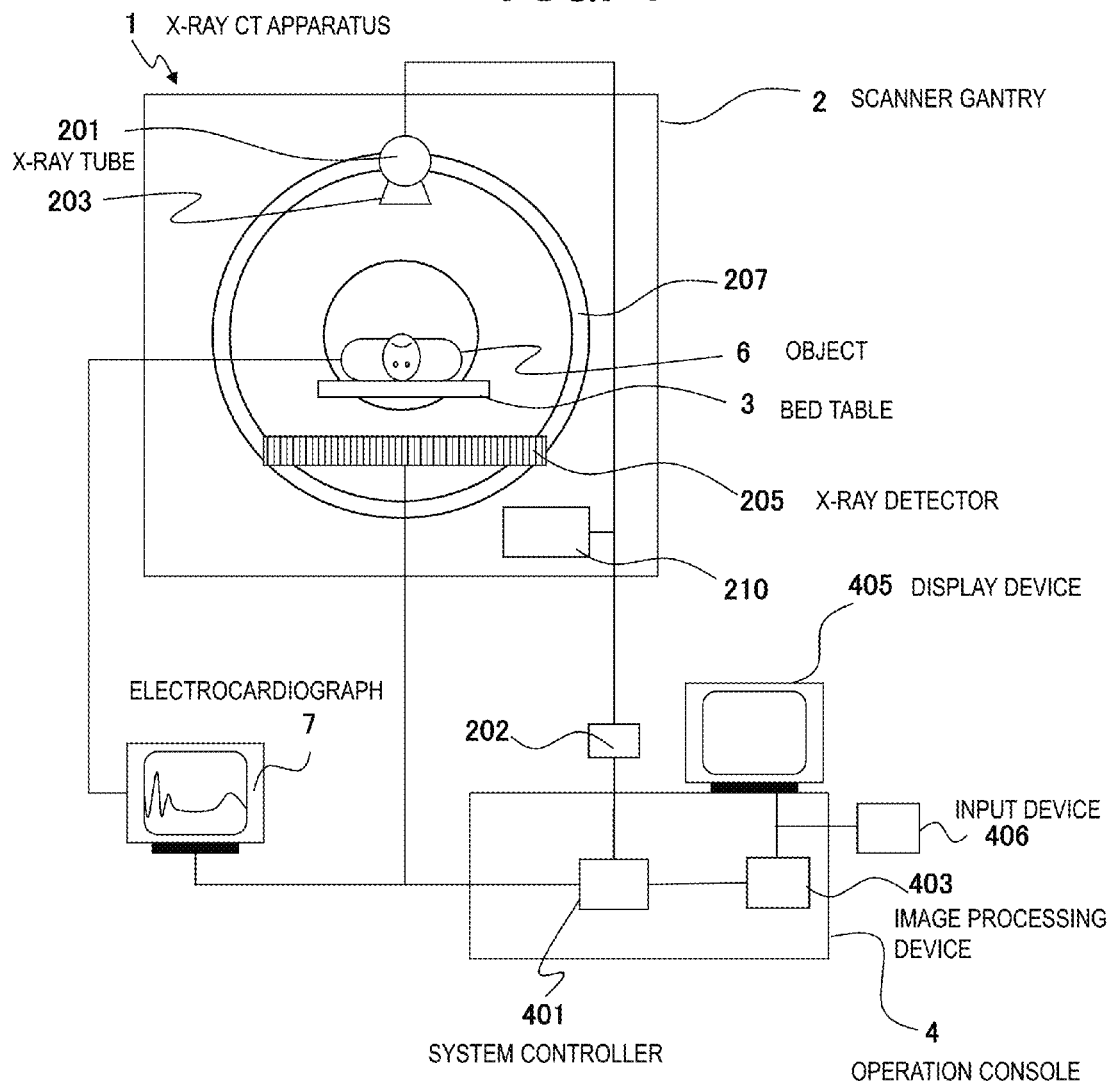
FIG. 1 is an overall configuration diagram of the X-ray CT apparatus 1.

First, referring to FIG. 1, the configuration of the X-ray CT apparatus 1 related to the present invention will be described.

The X-ray CT apparatus 1 irradiates an X-ray to the object 6 and comprises the scanner gantry 2 for detecting the X-ray transmitted through the object 6, the bed table 3 for placing the object 6, the measurement controller 202 for controlling the rotation operation and the X-ray irradiation of the scanner gantry 2, the electrocardiograph 7 for acquiring electrocardiac information of the object 6, and the operation console 4 for controlling each units of the X-ray CT apparatus 1. The operation console 4 comprises the system controller 401, the image processing device 403, the display device 405, and the input device 406.

The X-ray tube 201 as well as the collimator 203 and the X-ray detector 205 are disposed oppositely across an opening of the rotary disk 207 in the scanner gantry 2. The opening that is an X-ray irradiation space is provided for the rotary disk 207 in which the bed table 3 for placing the object 6 is carried. The rotary disk is driven so as to rotate around the object 6 by a driving force transmitted through a driving transmission system from the rotary driving device 210. The rotary driving device 210 is controlled by the measurement controller 202.

The X-ray tube 201 is an X-ray source controlled by the measurement controller 202 and irradiates an X-ray with a predetermined intensity continuously or intermittently. The measurement controller 202 controls an X-ray tube voltage and an X-ray tube current to be applied or supplied to the X-ray tube 201 according to the X-ray tube voltage and the X-ray tube current determined by the system controller of the operation console 4. The collimator 203 irradiates an X-ray emitted from the X-ray tube 201 to the object 6 as an X-ray such as a cone beam (a cone-or pyramid-shaped beam), the opening width of the collimator 203 is controlled by the measurement controller 202. The X-ray transmitted through the object 6 enters the X-ray detector 205.

An X-ray detection element group is composed by the combination of a scintillator and a photodiode for example, approximately 1,000 pieces of the X-ray detection element groups are arranged in the channel direction (circumferential direction) for example; approximately 1 to 320 pieces of the X-ray detection element groups are arranged in the column direction (body-axis direction) for example in the X-ray detector 205, and the X-ray detector 205 is disposed oppositely to the X-ray tube 201 across the object 6. The X-ray detector 205 detects an X-ray emitted from the X-ray tube 201 and transmitted through the object 6 and outputs the detected transmission X-ray data to a data collection device that is not shown in the diagrams. The data collection device collects transmission X-ray data to be detected by the respective X-ray detection elements of the X-ray detector 205, convert it into digital data, and then serially outputs it to the image processing device 403 of the operation console 4 as projection data.

The measurement controller 202 controls the rotation of the X-ray tube 201, the collimator 203, and the rotary disk 207 in the scanner gantry 2 according to the control signal from the system controller 401 of the operation console 4.

The bed table 3 properly controls the height of the bed table 3 according to the control signal sent from the system controller 401 of the operation console 4 and moves back and forth in the body-axis direction and in the direction vertical to the body axis and parallel to the top plate (horizontal direction). By the back-and-forth movement, the object 6 is carried in and out of the opening of the scanner gantry 2 (X-ray irradiation space).

The system controller 401 of the operation console 4 is a computer comprising a CPU (Central Processing Unit), a ROM (Read Only Memory), a RAM (Random Access Memory), a storage unit such as a hard disk, etc. The system controller 401 controls the scanner gantry 2 (the measurement controller 202), the bed table 3, and the electrocardiograph 7.

A storage unit of the system controller 401 stores images to be generated by the image processing device 403, a program to achieve the functions of the X-ray CT apparatus 1, etc.

The image processing device 403 performs pre-processing such as logarithmic transformation, sensitivity correction, etc. for the acquired projection data, and then reconstructs a tomographic image. The functional configuration of the image processing device 403 will be described later.

The display device 405 is composed of a display device such as a liquid crystal panel and a CRT monitor and a logic circuit to execute display processing in conjunction with the display device and is connected to the system controller 401. The display device 405 displays reconstruction images to be output from the image processing device 403 as well as various information to be handled by the system controller 401, and the display contents are viewed by an operator.

The input device 406 is composed of, for example, pointing devices such as a keyboard and a mouse, a numeric keypad, various switch buttons, etc. and outputs various commands and information to be input by an operator to the system controller 401. The operator interactively operates the X-ray CT apparatus 1 by using the display device 405 and the input device 406.

The electrocardiograph 7 measures electrocardiac information showing temporal changes of an action potential in which cardiac activity of the heart was reflected via through electrodes attached to the object 6. The electrocardiac information measured by the electrocardiograph 7 is serially transmitted to the system controller 401 and is added to the projection data by the system controller 401.

<First Embodiment>

Referring to FIGS. 2 to 11, the X-ray CT apparatus 1 of the first embodiment will be described.

First, the functional configuration of the image processing device 403 will be described.

Figure 2:
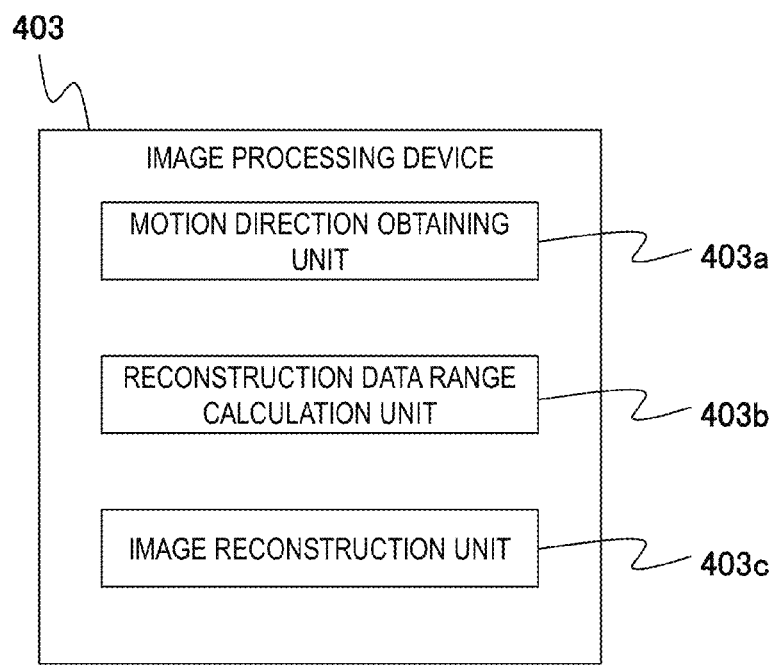
FIG. 2 is a functional block diagram of the image processing device 403 in the first embodiment.

As shown in FIG. 2, the image processing device 403 has the motion direction obtaining unit 403a, the reconstruction data range calculation unit 403b, and the image reconstruction unit 403c.

The motion direction obtaining unit 403a obtains a motion direction of a site to be scanned. A method to obtain a motion direction may be "manual setting" in which a motion direction is set by an operator and "automatic setting" in which the image processing device 403 detects a motion direction by analyzing motions of the site to be scanned based on projection data and images. In the first embodiment description, a case where an operator manually sets a motion direction will be described.

Here, "motion" means a periodic movement of an organism such as heart beats, for example.

Thoracic movement caused by respiration etc. is also included in "motion" mentioned in the present invention. Furthermore, "motion" to be a target of the present invention has a feature in which a motion amount is larger in a certain direction at a point. Specifically, for example, in case of the heart, a motion amount in the body-width direction (mediolateral direction of an object) is larger than that in the body-thickness direction (anteroposterior direction of an object). Also, in case of a lung, a motion amount in the body-thickness direction (anteroposterior direction of an object) is larger than that in the body-width direction (mediolateral direction of an object). Therefore, in the present invention, a direction where a motion amount is the largest at a point is referred to as "motion direction".

Figure 3:
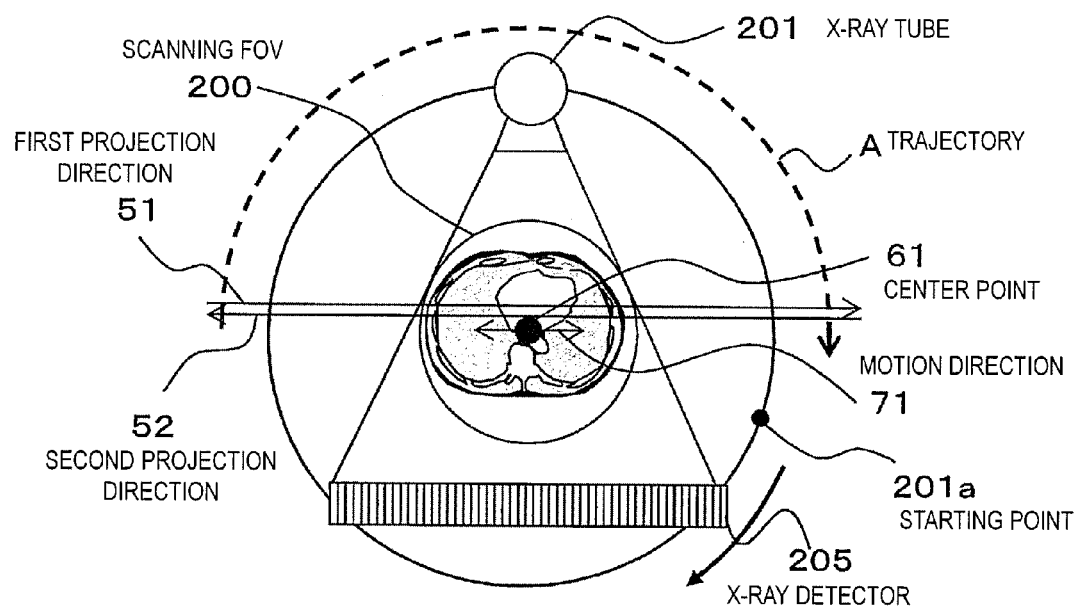
FIG. 3 is a diagram explaining the relationship between the motion direction and the projection directions (a normal scan).

FIG. 3 is an example where the X-ray CT apparatus 1 scans the heart as a site to be scanned. The heart motion is the largest in the mediolateral direction of an object (the both-direction arrow 71 in FIG. 3) at the center point 61.

The reconstruction data range calculation unit 403b calculates a range of projection data to be used for reconstruction based on a motion direction obtained by the motion direction obtaining unit 403a. The range of the projection data to be used for the reconstruction is referred to as the reconstruction data range 8. In a normal scan where projection data of a rotation of 360 degrees is acquired by irradiating an X-ray while the bed table 3 is still, projection data of 360 degrees is acquired by a scan (a slice). On the other hand, projection data of 180 degrees is used for reconstructing an image. In the present invention, the reconstruction data range 8 is projection data in a range of at least 180 degrees or more including a projection direction (an X-ray irradiation angle) approximately corresponding to a motion direction of a site to be scanned.

"Approximate correspondence" includes cases of perfect correspondence and slight deviation. Additionally, the deviation degree should be within a range where the effect of the present invention, i.e. motion artifact reduction is obtained. In case of perfect correspondence, the largest effect can be obtained, and as the deviation becomes larger, the effect becomes lower.

In FIG. 3 for example, the mediolateral direction of an object is set to the motion direction 71 by centering on the center point 61 of a site to be scanned. The reconstruction data range calculation unit 403b sets a range of at least 180 degrees (the range of the trajectory A) between the first projection direction (X-ray irradiation angle) 51 and the second projection direction (x-ray irradiation angle) 52 corresponding to the motion direction 71, as the reconstruction data range 8. In other words, a straight line passing through the center of a scanning FOV and vertical to the motion direction 71 is set as the reference line, and the reconstruction data range 8 is a projection data range whose projection direction is set as a range of respectively 90 degrees or more (180 degrees or more as the total) that are symmetrical in the circumferential direction from the reference line.

Additionally, "corresponding to a motion direction" means correspondence of an angle between the motion direction 71 and a projection direction. Therefore, the present invention can be applied also to a case where a site to be scanned is located in a position deviated from the center of a scanning FOV. In this case, a projection direction parallel to the motion direction is "a projection direction corresponding to a motion direction".

As described above, when setting a range of 180 degrees including the first projection direction 51 and the second projection direction 52 corresponding to the motion direction 71 as the reconstruction data range 8, an influence in a motion direction of a site to be scanned becomes the minimum in opposite positions (the first projection directions 51 and the second projection direction 52 of FIG. 3) that are temporally distant. That is, projection data in the first projection directions 51 and the second projection direction 52 is measured so that there is no motion. This results in that motion artifacts can be reduced.

Figure 4:
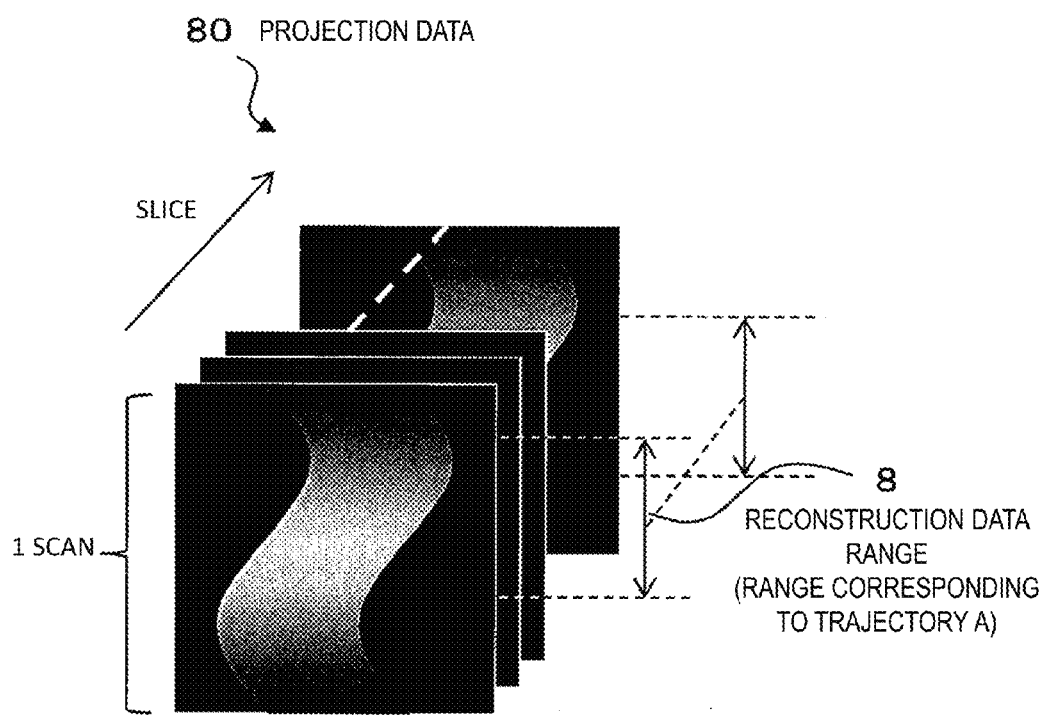
FIG. 4 is a diagram showing the reconstruction data range 8 in light of the motion direction.

The reconstruction data range 8 shown in FIG. 3 appears on the sinogram 80 of projection data as shown in FIG. 4. FIG. 4 is a sinogram in which the vertical axis is a projection direction (an X-ray irradiation angle) and the horizontal axis is a channel. Ranges of the both-direction arrows in FIG. 4 are the reconstruction data ranges 8. The reconstruction data range 8 is projection data of 180 degrees or more included in a scan and scanned between projection directions corresponding to the motion direction 71.

Generally, in an X-ray CT apparatus, an X-ray is irradiated in a fan-beam shape and is detected by an X-ray detector. Projection data shown in the present description and the diagrams shows projection data and angles in a case where an X-ray to be irradiated is not a fan-beam shape but a collimated beam. Therefore, it is natural to consider data required to convert an X-ray to be irradiated from a fan-beam shape to a collimated beam in case of considering a case where the X-ray to be irradiated is a fan-beam shape.

Additionally, the most suitable reconstruction data range 8 is projection data in a range of 180 degrees between the first projection directions (an X-ray irradiation angle) 51 and the second projection direction (X-ray irradiation angle) 52 corresponding to a motion direction of a site to be scanned as shown in FIG. 3.

Figure 5:
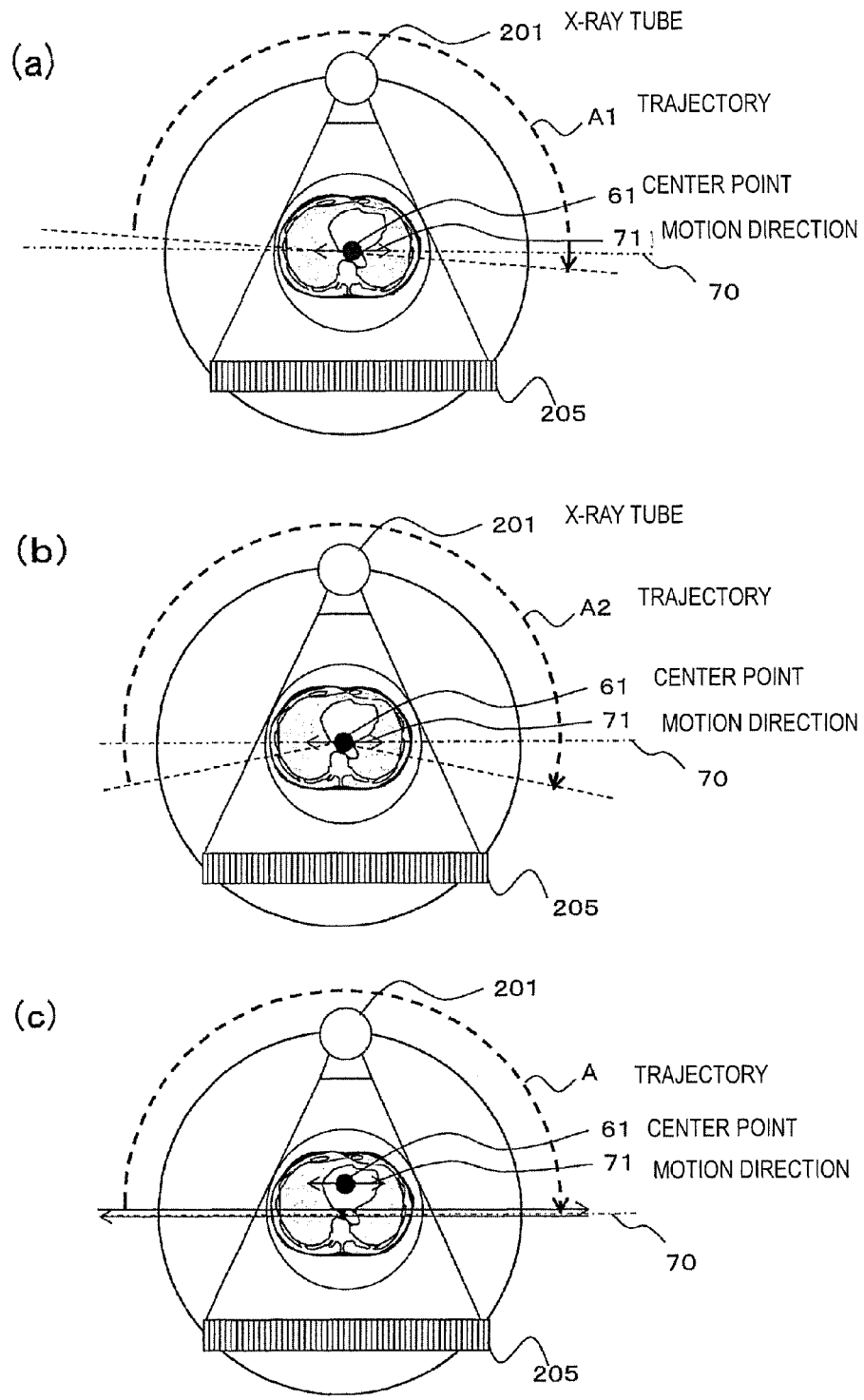
FIG. 5 is a variation example of the trajectory of an X-ray tube position corresponding to a reconstruction data range in light of the motion direction.

However, an effect of motion artifact reduction can be obtained also in various variations shown in FIG. 5.

For example, a projection direction being the upper and lower limits of a reconstruction data range may not perfectly correspond to a motion direction like a range of the trajectory A1 shown in FIG. 5(a).

Alternatively, a projection direction may be projection data of 180 degrees or more like a range of the trajectory A2 shown in FIG. 5(b). Even in this case, the effect of motion artifact reduction can be obtained.

Also, as described above, the motion center does not need to always correspond to the center of a scanning FOV as shown in FIG. 5(c). Even in this case, a projection data in a range of 180 degrees or more including the projection direction 70 approximately corresponding (parallel) to the motion direction is set as a reconstruction data range (a range corresponding to the trajectory A). Additionally, in a case where the motion center is not in the center of the scanning FOV, it is desirable to set projection data in a projection range in which a distance between the motion center (site to be scanned) and the X-ray source is closer, as the reconstruction data range. This is because a scanning time equivalent to projection data of 180 degrees is shorter in a position of a site to be scanned when an orbit of the X-ray tube 201 is closer to the site to be scanned.

The image reconstruction unit 403c uses projection data of the reconstruction data range 8 calculated by the reconstruction data range calculation unit 403b to reconstruct an image. For example, the iterative approximation method and the like are used for image reconstruction.

Figure 6:
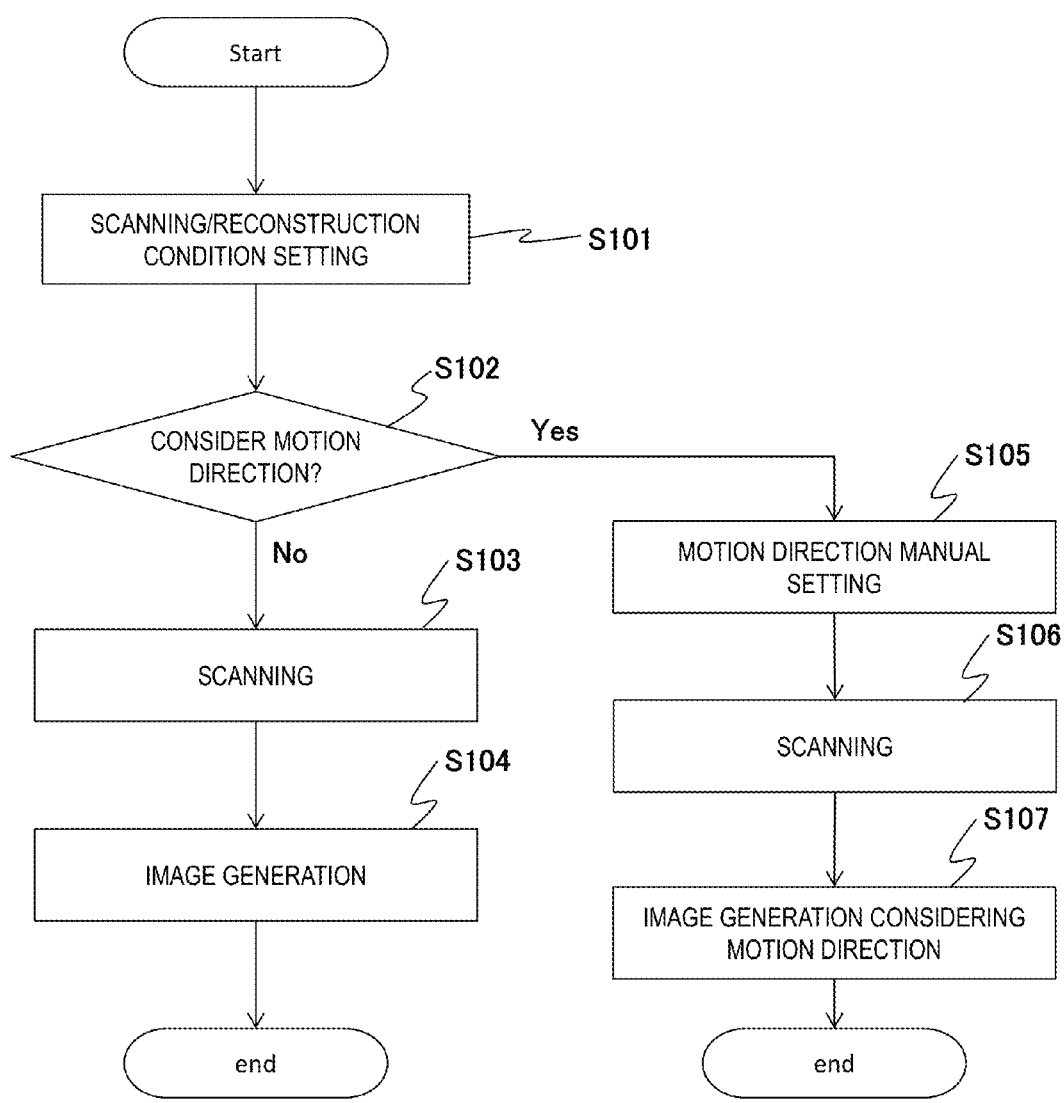
FIG. 6 is a flow chart explaining the flow of an image reconstruction process related to the present invention (the first embodiment).

Next, referring to FIG. 6, an image reconstruction process to be executed by the X-ray CT apparatus 1 will be described. The X-ray CT apparatus 1 of the present embodiment executes the image reconstruction process using the procedure shown in the flow chart of FIG. 6. That is, the CPU of the system controller 401 reads out a program and data of the image reconstruction process shown in FIG. 6 from a storage unit and executes the process based on the program and data.

First, the X-ray CT apparatus 1 performs settings such as scanning conditions and reconstruction conditions according to the operation by an operator (Step S101). The system controller 401, for example, displays the condition setting window 9 shown in FIG. 7 on the display device 405.

The scanogram image 91 and the cross-sectional model diagram 92 are displayed on the condition setting window 9. Additionally, the scanogram image 91 is acquired by a scanning process referred to as scanogram scanning in which an X-ray is irradiated while the X-ray tube 201 is being fixed to acquire an image in the body-axis direction after moving the bed table 3. Also, the condition setting area 96 for setting various scanning conditions and reconstruction conditions, the normal reconstruction button 97, the motion direction consideration reconstruction button 98, the start scanning button 99, the manual button 101, the DB button 102, the Raw button 103, the Img button 104, etc. are provided. Additionally, the condition setting window 9 is an example, and the window configuration, buttons to be arranged, etc. are not limited to the example of FIG. 7.

The condition setting area 96 is an operation region for setting, for example, a scanning type, a scanning range, a site to be scanned, a posture, the number of scans, a scanning time, a scanning FOV, an image thickness, a reconstruction filter, a reconstruction FOV, and scanning conditions/reconstruction conditions such as a reconstruction method. A plurality of buttons for entering input screens for various conditions are arranged in the condition setting area 96. The system controller 401 displays an input screen for a corresponding condition when a button in the condition setting area 96 is pressed down and receives an input of the condition. It may be configured so that a scanning range is set on the scanogram image 91.

The normal reconstruction button 97 is a button to be selected when performing a normal image reconstruction process that does not consider a motion direction. The motion direction consideration reconstruction button 98 is a button to be selected when performing an image reconstruction process that considers a motion direction.

The manual button 101, the DB button 102, the Raw button 103, and the Img button 104 are buttons that can be operated while the motion direction consideration reconstruction button 98 is being selected. The manual button 101 is to be operated when an operator inputs a motion direction and a motion center. When the manual button 101 is selected, the system controller 401 displays the motion direction manual setting window 9a shown in FIG. 8. The DB button 102 is selected when determining a motion direction by referring to a motion direction database (see FIG. 13; the second embodiment) to be described later. The Raw button 103 is operated to automatically detect a motion direction of a site to be scanned by analyzing projection data (the third embodiment). The Img button 104 is operated to automatically detect a motion direction of a site to be scanned by analyzing an image (the third embodiment).

The start scanning button 99 is a button that can be selected after setting scanning conditions, a reconstruction process, etc. When the start scanning button 99 is operated, the system controller 401 starts scanning based on the set scanning conditions etc.

Figure 7:
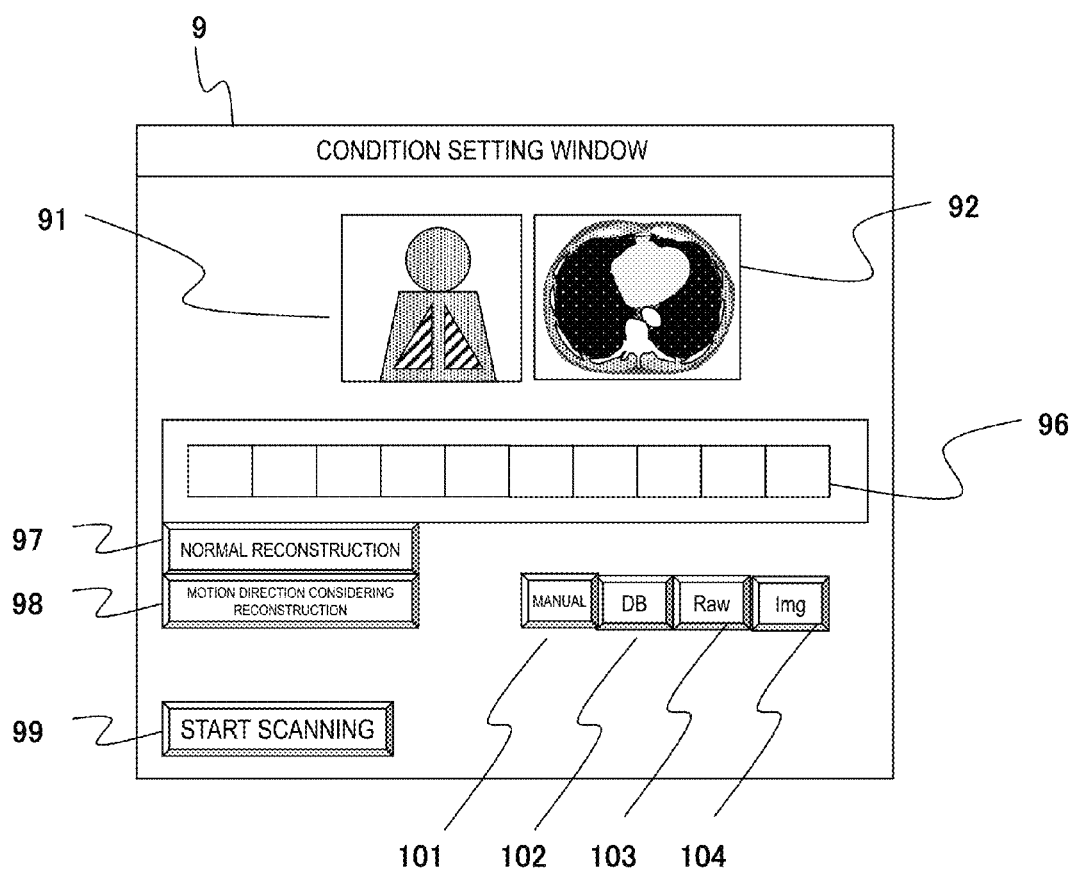
FIG. 7 is an example of the condition setting window 9.

On the condition setting window 9 shown in FIG. 7, scanning conditions and reconstruction conditions are set (Step S101), the normal reconstruction button 97 is pressed down (Step S102: No), the start scanning button 99 is pressed down, and then the system controller 401 starts a normal scanning process (Step S103). In a scanning process, the system controller 401 controls the respective parts of the scanner gantry 2 and the bed table 3 according to the scanning conditions set in Step S101.

For example, when performing a normal scan as shown in FIG. 3, an X-ray is irradiated while the bed table 3 is still to acquire projection data of a rotation of 360 degrees. The projection data of a rotation of 360 degrees is intermittently acquired in the same position by moving the bed table 3 by the set amount or without moving the bed table 3.

Also, the system controller 401 transmits projection data acquired by scanning to the image processing device 403. The image processing device 403 reconstructs a tomographic image of the object 6 based on the acquired projection data (Step S104).

On the other hand, when the motion direction consideration reconstruction button 98 and the manual button 101 are selected on the condition setting window 9 (Step S102: Yes), the system controller 401 displays the motion direction manual setting window 9a shown in FIG. 8 on the display device 405. An operator sets a motion direction and the motion center in the motion direction manual setting window 9a (Step S105).

Figure 8:
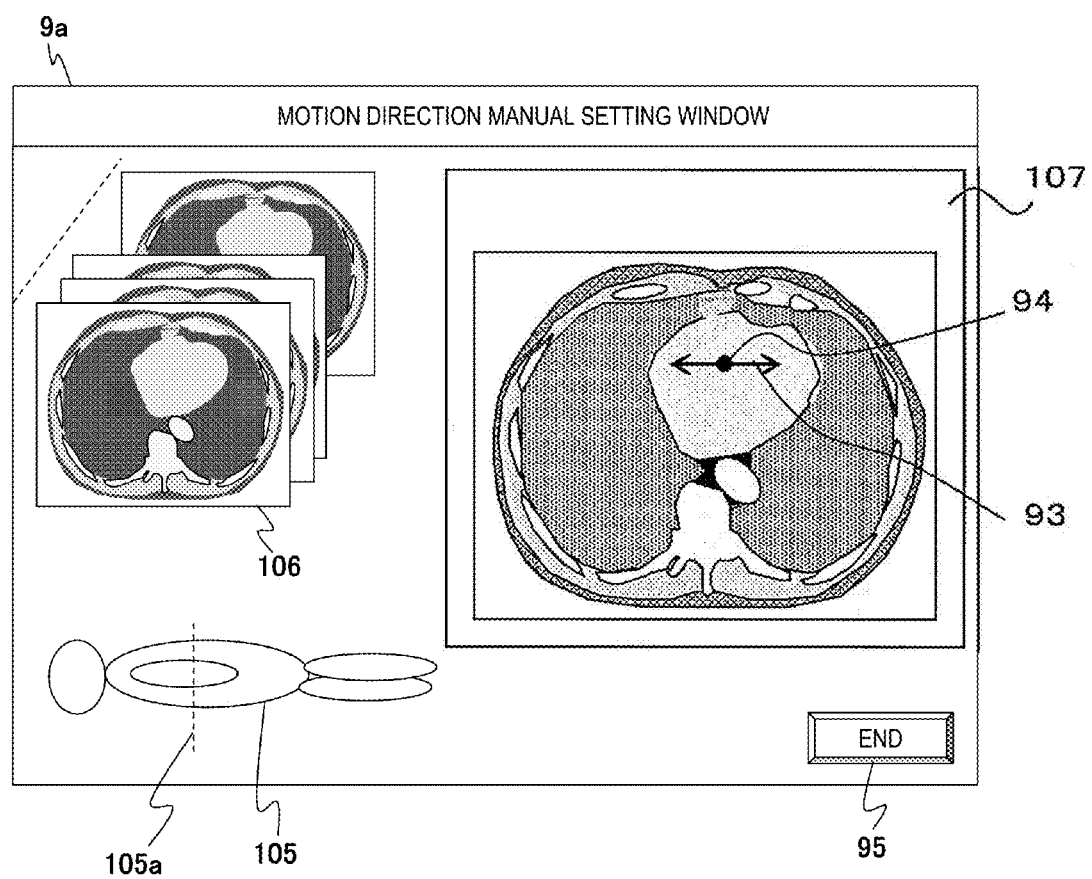

As shown in FIG. 8, the image 107 according to the scanning range (scanning position) set in Step S101 is displayed in the motion direction manual setting window 9a. The motion direction line 97 and the motion center mark 94 are displayed in the image 107. If a measured image of the same object is stored in the storage unit by reference scanning and the like, the measured image is desirably used as the image 107. If a measured image is not stored, a model diagram etc. of a site to be scanned may be used. Also, the serial images 106 for selecting the image 107 to set a motion direction and the object overall image 105 may be displayed. By moving the scanning position line 105a on the object overall image 105 or selecting an image in a desired slice position of the serial images 106, the motion direction setting image 107 to be displayed in the motion direction manual setting window 9a can be selected.

An angle of the motion direction line 93 can be changed by an operator. Also, a position of the motion center mark 94 can be changed by an operator. An operator changes an angle and a position of the motion direction line 93 and the motion center mark 94 using the input device 406 such as a mouse. When the end button 95 is pressed down, the image processing device 403 acquires an set angle that the motion direction line 93 shows and a position designated by the motion center mark 94. Then, the motion direction manual setting window 9a is closed, and the condition setting window 9 reappears.

When the start scanning button 99 on the condition setting window 9 is pressed down, the system controller 401 first performs a scanning process similarly to Step S103 (Step S106). That is, the system controller 401 controls the respective parts of the scanner gantry 2 and the bed table 3 according to the scanning conditions set in Step S101. The system controller 401 transmits projection data acquired by scanning to the image processing device 403.

When the image processing device 403 acquires the projection data, a motion direction set in Step S105 is considered to reconstruct a tomographic image of an object (Step S107).

In the image generation process of Step S107, the image processing device 403 sets projection data in a projection range of at least 180 degrees including a projection direction approximately corresponding to a motion direction set in Step S105, as the reconstruction data range 8. Additionally, in a normal scan, a position (the start position 201a) of the X-ray tube 201 when scanning starts is set so that the position is not included in the reconstruction data range 8. This is because a normal scan performing scanning by only one rotation results in that reconstruction is performed using temporally discontinuous projection data if the reconstruction data range 8 exceeds the start position 201a.

The image processing device 403 uses projection data of the reconstruction data range 8 to perform an image reconstruction process according to the reconstruction conditions. The image processing device 403 displays the generated image on the display device 405, stores it in the storage unit of the system controller 401, and then ends the present image reconstruction process.

As described above, the X-ray CT apparatus 1 of the first embodiment reconstructs an image using projection data in a range of 180 degrees or more including a projection direction approximately corresponding to a motion direction of a site to be scanned. Hence, an image can be reconstructed using projection data in which influence in a motion direction of a scanning target site becomes the minimum between temporally distant projection data. Therefore, an image in which motion artifacts are reduced can be generated.

Additionally, although the example where an image reconstruction process that considers a motion direction for a normal scan is applied is shown above, the other scan types can also be applied. For example, the present invention can be applied also to a continuous dynamic scan in which the same body-axis direction position is continuously scanned while the bed table 3 is still to generate a different image from projection data continuous in the time-axis direction, a spiral scan (volume scan) in which X-rays are continuously irradiated while the bed table 3 is being moved using a multi-slice CT apparatus, etc.

(Continuous Dynamic Scan)

Figure 9:
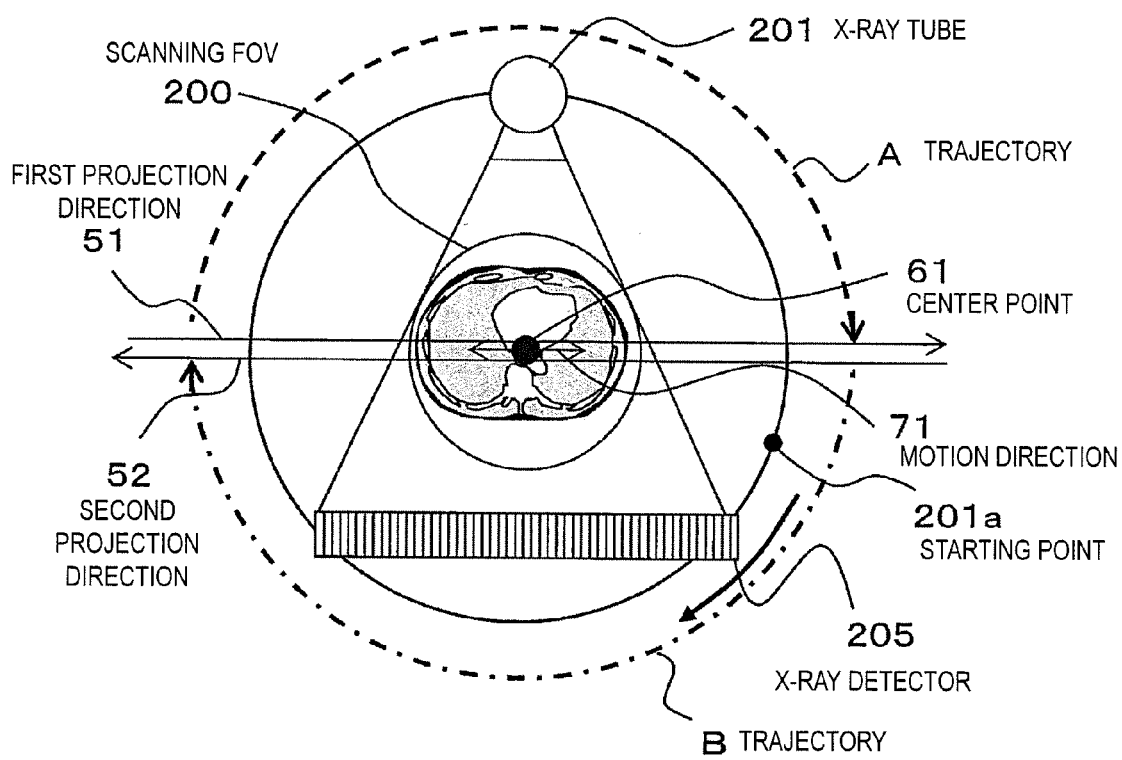
FIG. 9 is a diagram explaining a reconstruction data range from the view point of an X-ray irradiation angle in a continuous dynamic scan.
Figure 10:
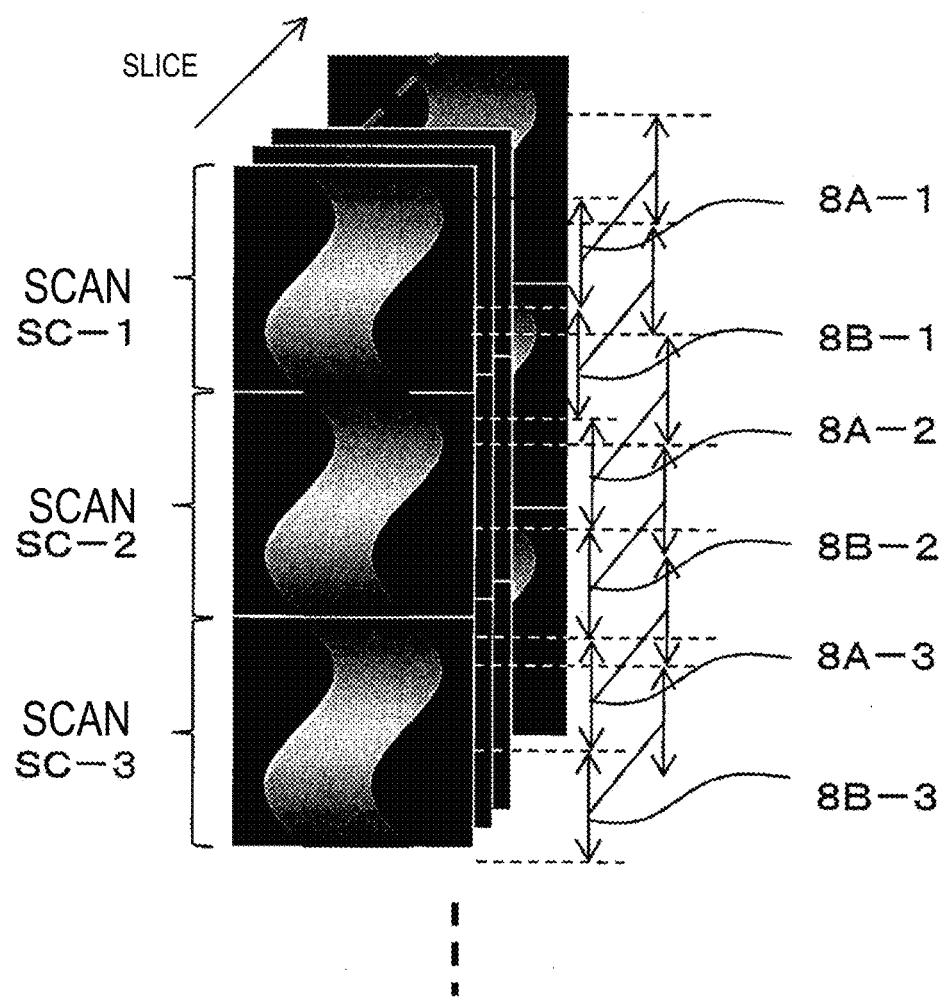
FIG. 10 is a diagram explaining the respective reconstruction data ranges 8A-1, 8B-1, . . . corresponding to the trajectories A and B of FIG. 9.

FIG. 9 is a diagram explaining a reconstruction data range in a continuous dynamic scan, and FIG. 10 is a diagram showing reconstruction data ranges in the continuous dynamic scan of FIG. 9 on projection data (a sinogram).

Also in a continuous dynamic scan, motion artifacts can be reduced by setting projection data in a range of 180 degrees or more including a projection direction approximately corresponding to a motion direction of a site to be scanned as a reconstruction data range as described above. Additionally, there is no problem even if the reconstruction data range exceeds the starting point 201a of X-ray irradiation in the continuous dynamic scan.

The trajectories A and B in FIG. 9 are trajectories of the X-ray tube 201 corresponding to the respective reconstruction data ranges. In "projection data in a range of 180 degrees or more including a projection direction approximately corresponding to a motion direction of a site to be scanned", there are at least two patterns of ranges: the first reconstruction data range 8A obtained using the trajectory A that does not exceed the starting point 201a and the second reconstruction data range 8B obtained using the trajectory B that inverted the trajectory A. The trajectory B corresponding to the second reconstruction data range 8B exceeds the starting point 201a.

In case of a continuous dynamic scan, the first reconstruction data range 8A and the second reconstruction data range 8B may be adopted similarly to FIG. 3 (a case of a normal scan). This is because a continuous dynamic scan continuously performs a plurality of scans for the same slice position to keep continuity of projection data between scans. In particular, this is effective in case of examining dynamics of a site to be scanned.

(Spiral Scan Using a Multi-slice CT Apparatus)

FIG. 11 shows a reconstruction data range in case of performing a spiral scan using a multi-slice CT apparatus on projection data (a sinogram). In a spiral scan, X-rays are irradiated continuously while moving the bed table 3.

In case of performing a reconstruction process without considering a motion direction, the image processing device 403 conventionally collects projection data of at least 180 degrees by centering an angle at which a position of an image to be generated and a center slice correspond as shown in FIG. 11(a) to reconstructs an image. Data in a proper position is collected for reconstruction by using projection data of a forward slice before the center angle and that of a backward slice after the center angle. The respective projection data 81A to 81I shown in the both-direction arrows in FIG. 11(a) is used for reconstructing one tomographic image.

On the other hand, the present invention uses projection data in a range of 180 degrees or more including a projection direction approximately corresponding to a motion direction of a site to be scanned for reconstruction from among the above projection data 81A to 81I as shown in FIG. 11(b). That is, the reconstruction data range indicates the ranges 82A to 82I shown in the both-direction arrows of solid lines in FIG. 11(b).

In FIG. 11(b), the reconstruction data ranges 82A to 82C, 82D to 82F, and 82G to 82I become projection data acquired in the same projection angle range respectively.

Also, although projection data in a range of 180 degrees or more including a projection direction approximately corresponding to a motion direction of a site to be scanned has two directions, more effects can be obtained when using projection data in which a trajectory of the X-ray tube 201 and a site to be scanned are closer.

<Second Embodiment>

Next, referring to FIGS. 12 to 14, the second embodiment will be described in detail.

Figure 12:
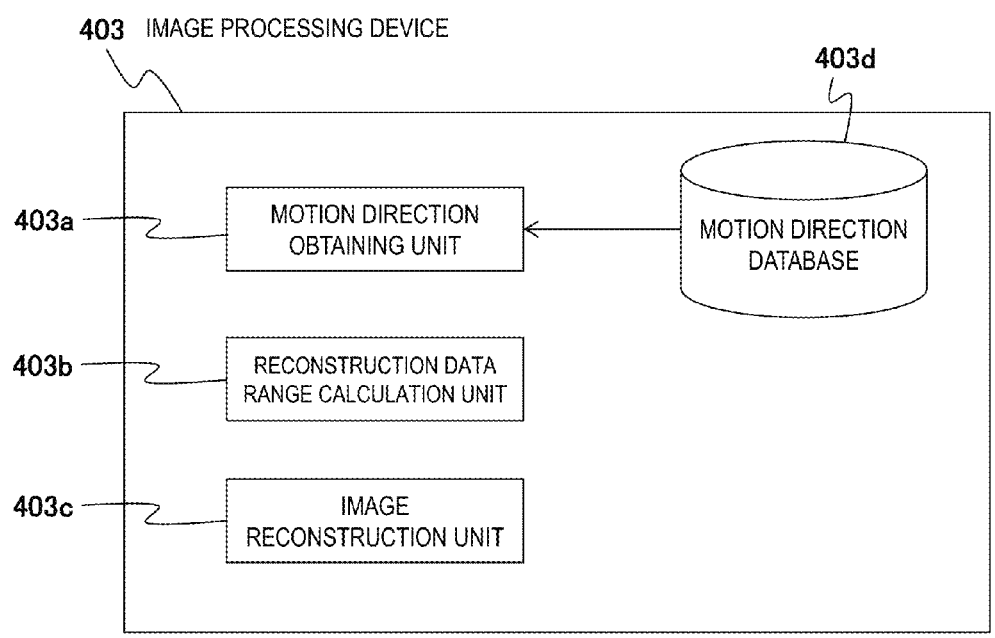
FIG. 12 is a functional block diagram of the image processing device 403 of the second embodiment.

FIG. 12 is a diagram showing the functional configuration of the image processing device 403 in the second embodiment.

As shown in FIG. 12, the image processing device 403 of the second embodiment has the motion direction obtaining unit 403a, the reconstruction data range calculation unit 403b, the image reconstruction unit 403c, and the motion direction database 403d.

That is, in the second embodiment, the motion direction database 403d is provided in addition to the functional configuration of the first embodiment shown in FIG. 2. The motion direction database 403d is held in the storage unit in advance.

Figure 13:
FIG. 13 is an example of the motion direction database 403d.

As shown in FIG. 13, information about motion directions according to the site to be scanned and the postures is stored in the motion direction database 403d. For example, a motion direction is in the horizontal direction in a case where the site to be scanned is the heart; the posture is supine, and a motion direction is in the vertical direction in a case where the site to be scanned is the heart; the posture is recumbent. A motion direction is in the vertical direction in a case where the site to be scanned is the thorax (lungs); the posture is supine, and a motion direction is in the horizontal direction in a case where the site to be scanned is the thorax (lungs); the posture is recumbent.

The motion direction obtaining unit 403a of the image processing device 403 obtains a motion direction according to the site to be scanned and the posture by referring to the motion direction database 403d. Then, a range of projection data (reconstruction data range) to be used for reconstructing an image is calculated based on the obtained motion information. Additionally, the site to be scanned and the posture have been set as scanning conditions.

Additionally, in the following descriptions, the same symbols are provided for the parts similar to those shown in FIGS. 1 and 2, and the repeated explanations are omitted.

Figure 14:
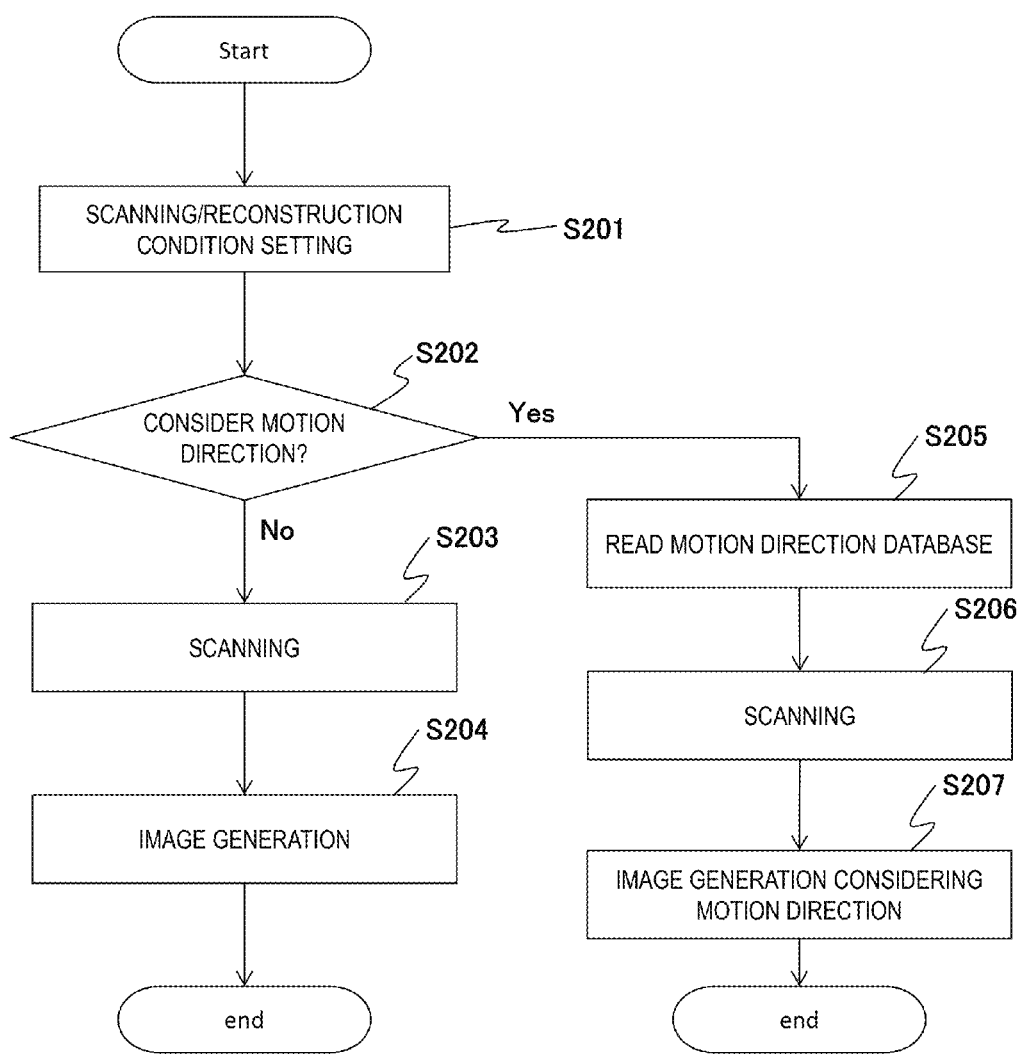
FIG. 14 is a flow chart explaining the flow of an image reconstruction process related to the present invention (the second embodiment).

Referring to FIG. 14, an image reconstruction process that the X-ray CT apparatus 1 of the second embodiment executes will be described.

First, the X-ray CT apparatus 1 performs setting for scanning conditions and reconstruction conditions according to the operation by an operator (Step S201). Setting the scanning conditions and reconstruction conditions is performed on the condition setting window 9 shown in FIG. 7 similarly to Step S101 of FIG. 6.

Additionally, because the process without considering a motion direction in Step S202 (Step S202: No to Step S204) is similar to that in Step S102: No to Step S104 of the first embodiment, the explanation will be omitted.

In the condition setting window 9 (FIG. 7), when scanning conditions and reconstruction conditions are set (Step S201); the motion direction considering reconstruction button 98 is selected; and additionally the DB button 102 is selected (Step S202: Yes), the system controller 401 loads the motion direction database 403d shown in FIG. 13 to determine a motion direction in accordance with a site to be scanned and a posture (Step S205). The system controller 401 transmits the determined motion direction to the image processing device 403.

Then, when the start scanning button 99 on the condition setting window 9 is pressed down, the system controller 401 performs a scanning process (Step S206). That is, the system controller 401 controls the respective parts of the scanner gantry 2 and the bed table 3 according to the scanning conditions set in Step S201. The system controller 401 transmits projection data acquired by scanning to the image processing device 403.

After acquiring the projection data, the image processing device 403 considers the motion direction determined in Step S205 to reconstruct a tomographic image of an object (Step S207). The image processing device 403 reconstructs an image by setting projection data in a projection range of at least 180 degrees or more including a projection direction approximately corresponding to a motion direction as the reconstruction data range 8. The image processing device 403 displays an image reconstructed in Steps S204 and S207 on the display device 405, stores it in the storage unit of the system controller 401, and then ends the present image reconstruction process.

The process of the second embodiment can be applied to any of a normal scan, a continuous dynamic scan, and a volume scan described in the first embodiment.

As described above, in the second embodiment, the X-ray CT apparatus 1 stores the motion direction database 403d in advance, which can obtain a motion direction according to the site to be scanned and the posture from the motion direction database 403d. Therefore, an operator does not need to set a motion direction manually, which results in that image reconstruction considering a motion direction can be performed with an easier operation.

<Third Embodiment>

Figure 15:
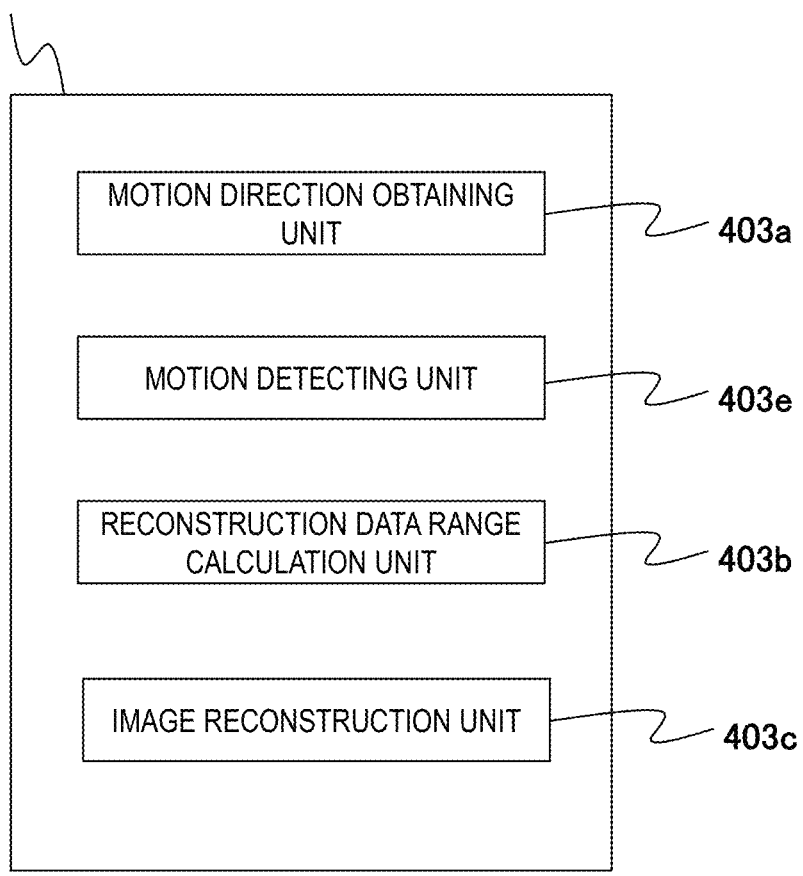
FIG. 15 is a functional block diagram of the image processing device 403 of the third embodiment.

Next, referring to FIGS. 15 to 19, the third embodiment will be described in detail. FIG. 15 is a diagram showing the functional configuration of the image processing device 403 of the third embodiment.

As shown in FIG. 15, the image processing device 403 of the third embodiment has the motion direction obtaining unit 403a, the motion detecting unit 403e, the reconstruction data range calculation unit 403b, and the image reconstruction unit 403c.

That is, in the third embodiment, the motion detecting unit 403e is provided in addition to the functional configuration of the first embodiment shown in FIG. 2.

The motion detecting unit 403e detects a motion direction of a site to be scanned. For example, the following two methods of detecting a motion direction can be considered.

(a) a method to calculate based on a difference between the respective projection data in opposite projection directions (b) a method to calculate based on a difference between images of the same site reconstructed by shifting a projection data range to be used for reconstruction The specific calculation method for a motion direction will be described later.

The motion direction obtaining unit 403a of the image processing device 403 obtains a motion direction calculated by the motion detecting unit 403e and transmits it to the reconstruction data range calculation unit 403b. The reconstruction data range calculation unit 403b calculates a range of projection data (reconstruction data range) to be used for reconstructing an image based on the obtained motion direction.

Figure 16:
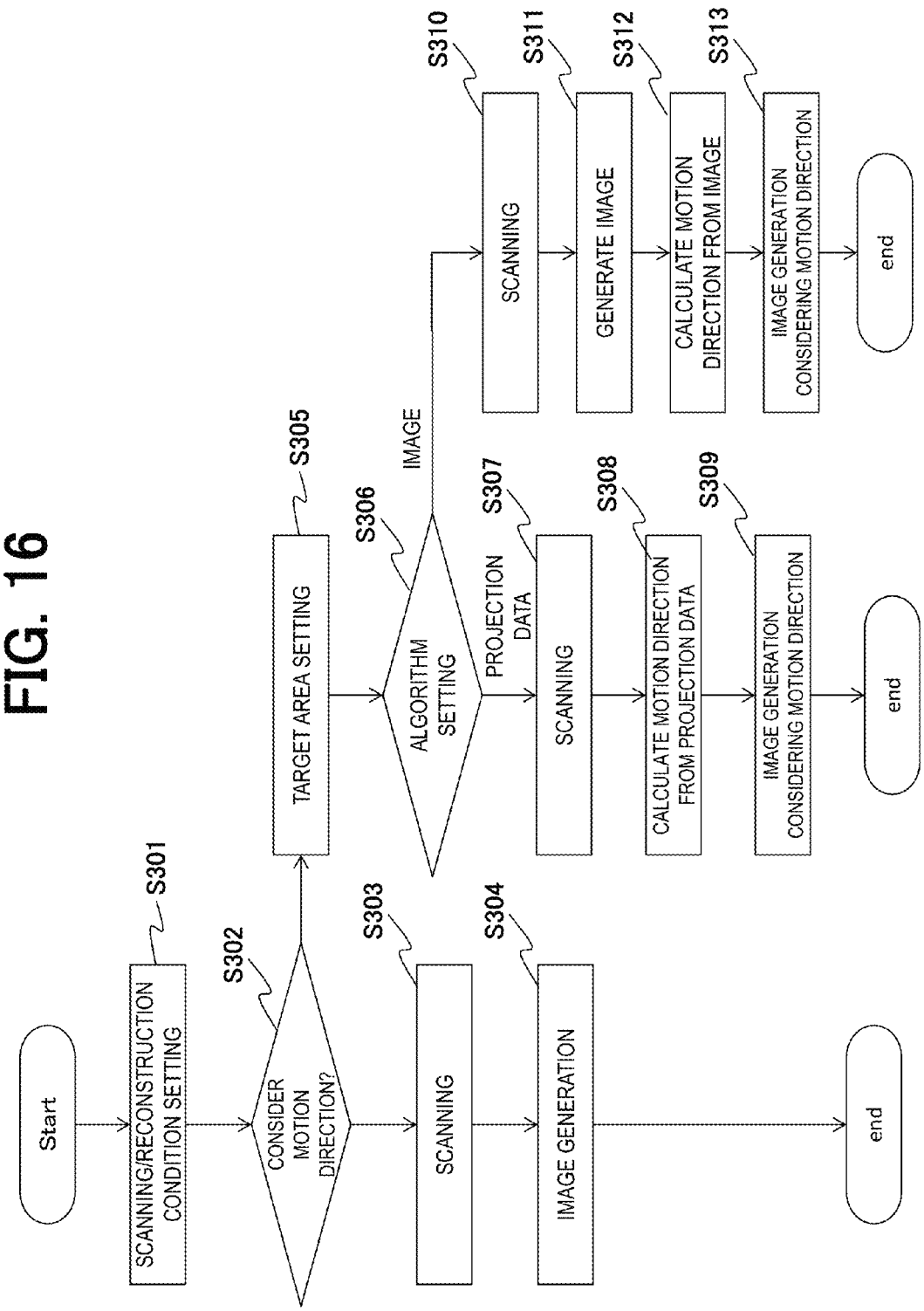
FIG. 16 is a flow chart explaining the flow of an image reconstruction process related to the present invention (the third embodiment).

Referring to FIG. 16, an image reconstruction process executed by the X-ray CT apparatus 1 of the third embodiment will be described.

First, the X-ray CT apparatus 1 performs setting for scanning conditions and reconstruction conditions according to the operation by an operator (Step S301). Setting the scanning conditions and reconstruction conditions is performed on the condition setting window 9 (FIG. 7) similarly to Step S101 of FIG. 6.

Additionally, because the process without considering a motion direction in Step S302 (Step S302: No to Step S304) is similar to that in Step S102: No to Step S104 of the first embodiment, the explanation will be omitted.

In the condition setting window 9, when scanning conditions and reconstruction conditions are set (Step S301); the motion direction considering reconstruction button 98 is selected; and additionally the Raw button 103 or the Img button 104 is selected (Step S302: Yes), the system controller 401 displays the motion direction automatic setting window 9c shown in FIG. 17 on the display device 405. An operator sets a target area where motion information is detected using the motion direction automatic setting window 9c (Step S305).

Figure 17:
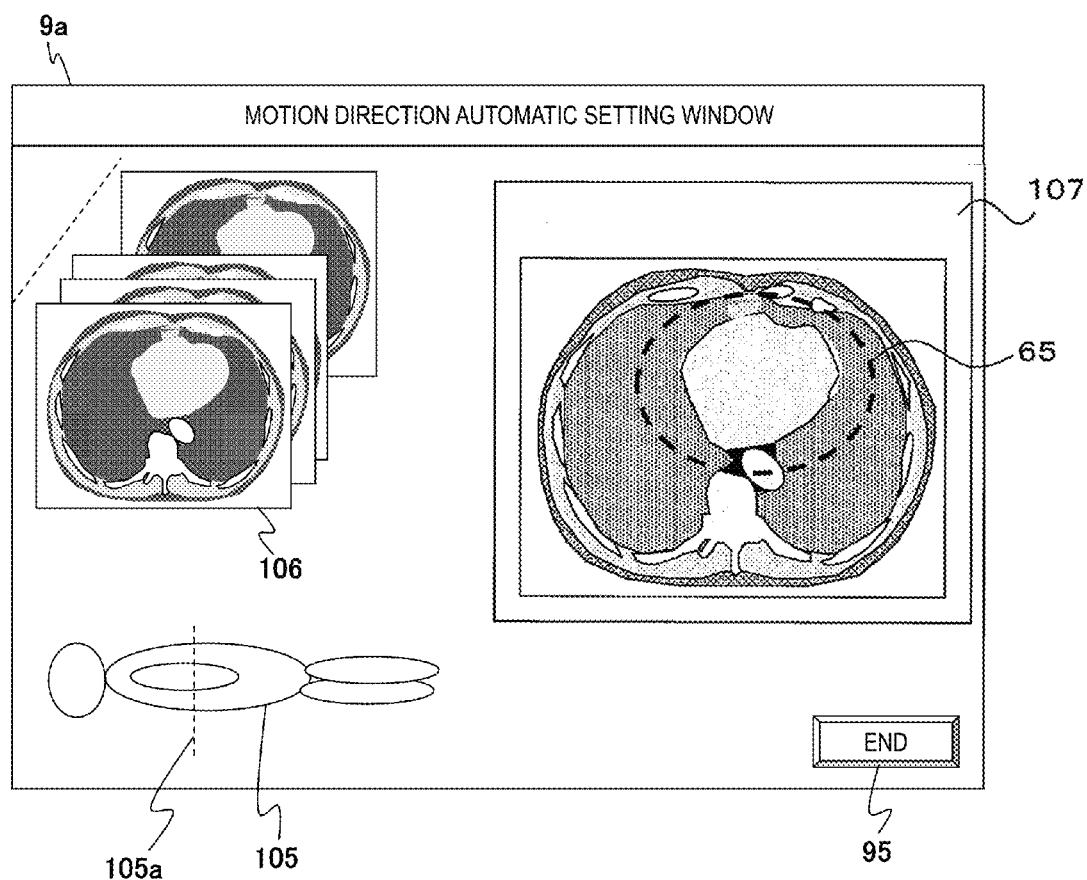
FIG. 17 is an example of the motion direction automatic setting window 9c.

As shown in FIG. 17, the motion direction automatic setting window 9c displays the image 107 according to the scanning range (scanning position) set in Step S301. The target area setting frame 65 is displayed in the image 107.

The size and position of the target area setting frame 65 can be changed by an operator's operation.

Also, the shape of target area setting frame 65 is not limited to an oval shape as shown in FIG. 17 but may be a rectangle, a circle, or the other arbitrary shapes. An operator changes the position and size of the target area setting frame 65 using the input device 406 such as a mouse to select a desired site. The selected site is designated as an analysis target for motion information. When the end button 95 is pressed down, the image processing device 403 obtains a position and size of the set target area 65, closes the motion direction automatic setting window 9c, and then goes back to the condition setting window 9.

Next, the image processing device 403 checks a set motion detection algorism (motion detection method), and the process proceeds according to the set algorism. When the Raw button 103 is selected on the condition setting window 9, the motion detection algorism (the above motion detection method of (a)) is executed based on projection data analysis (Step S306: PROJECTION DATA). On the other hand, when the Img button 104 is selected on the condition setting window 9, the motion detection algorism (the above motion detection method of (b)) is executed based on image analysis (Step S306: IMAGE).

In either case, a scanning process is first performed (Steps S307 and S310). The scanning process starts when the start scanning button 99 on the condition setting window 9 is pressed down. The scanning process is similar to the scanning process etc. in Step S103 of the first embodiment.

Figure 18:
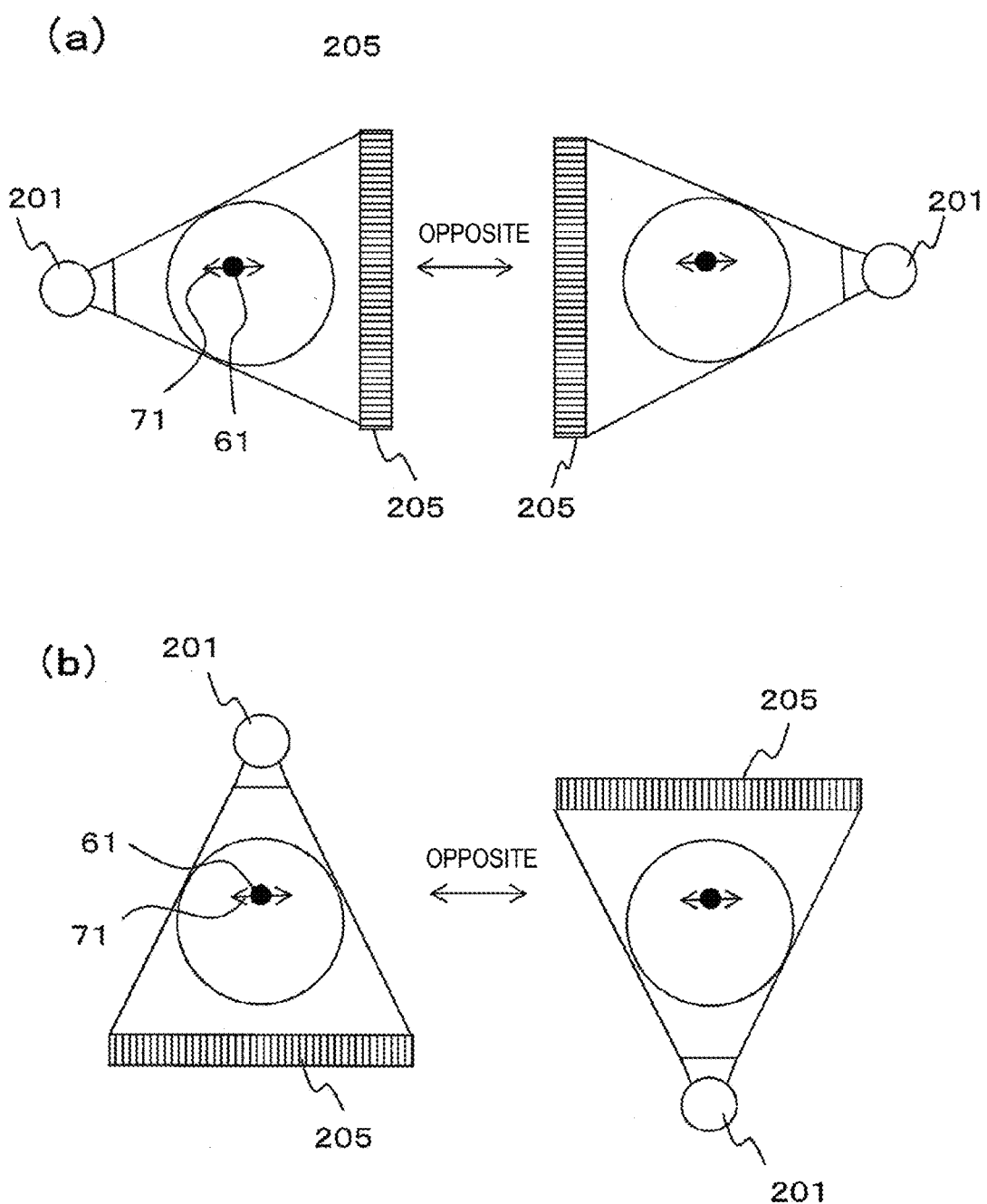
FIG. 18 is a diagram explaining motion direction detection based on projection data.

When the Raw button 103 is selected on the condition setting window 9, the image processing device 403 acquires projection data to calculate a motion direction based on the projection data (Step S308). As a method to calculate a motion direction from the projection data, for example, there is a method to compare opposite data. As shown in FIG. 18, the opposite data is projection data whose projection direction is inverted by 180 degrees. The image processing device 403 obtains a difference of the opposite data and calculates a motion direction based on a size of the difference.

FIG. 18(a) is a diagram showing the arrangement of the X-ray tubes 201 in case of opposite data whose direction corresponds to the motion direction 71. A difference by motion becomes small between the opposite data in case of the opposite data whose projection direction corresponds to a motion direction. On the other hand, as shown in FIG. 18(b), a difference by motion becomes large between the opposite data in case of the projection data whose direction is vertical to the motion direction 71.

The image processing device 403 obtains differences at various angles to calculate an angle of opposite data with the minimal difference as a motion direction.

Additionally, in a case where a target area is set (see FIG. 17), it may be configured so that a difference of opposite data is calculated by setting the target area only as a calculation target. Because only the target area is calculated, the range is narrowed down, which can perform high-speed processing.

The image processing device 403 reconstructs an image by setting projection data in a projection range of at least 180 degrees or more including a projection direction approximately corresponding to a motion direction calculated in Step S308 as the reconstruction data range 8 (Step S309).

When the Img button 104 is selected on the condition setting window 9, the image processing device 403 generates a plurality of analysis images based on the acquired projection data (Step S311).

FIG. 19 is a diagram explaining an analysis image.

As shown in FIG. 19(a), a range of at least 180 degrees to be used for reconstruction is cut out of projection data by shifting the range gradually. An image reconstructed using projection data of the range 83A shown in FIG. 19(a) is the analysis image 84A of FIG. 19(b). An image reconstructed using projection data of the range 83B slightly shifted from the range 83A is the analysis image 84B of FIG. 19(b). Similarly, the analysis images 84C to 84F are generated by gradually shifting a projection data range to be used. The range 83D is the opposite data of the range 83A, the range 83E is the opposite data of the range 83B, and the range 83F is the opposite data of the range 83C.

As shown in FIG. 19(b), the image processing device 403 obtains a difference between the analysis images 84A and 84D reconstructed by opposite data. Similarly, a difference between the analysis images 84B and 84E and a difference between the analysis images 84C and 84F are obtained respectively. Then, a projection direction of an analysis image with the minimal difference at an opposite angle is set as a motion direction (Step S312).

Additionally, in a case where a target area is set (see FIG. 17), only the target area may be set as a target for difference calculation. That is, the image processing device 403 calculates a difference of opposite images only for pixels in the target area. Because the calculation range is narrowed down, high-speed processing can be performed.

The image processing device 403 reconstructs an image by setting projection data in a projection range of at least 180 degrees or more including a projection direction approximately corresponding to a motion direction calculated in Step S312 as the reconstruction data range 8 (Step S313).

The image processing device 403 displays images reconstructed in Steps S304, S309, and S313 on the display device 405, stores them in the storage unit of the system controller 401, and then ends the present image reconstruction process.

The process of the third embodiment can be applied to any of a normal scan, a continuous dynamic scan, and a volume scan described in the first embodiment.

As described above, in the third embodiment, the X-ray CT apparatus 1 can detect a motion direction based on projection data obtained by scanning or a reconstructed image. Therefore, an operator does not need to set a motion direction manually. Also, because a motion of a site to be scanned is analyzed based on scanned projection data of an object itself, a motion direction can be obtained accurately.

Additionally, although a case of generating an image from projection data at the same time as a scanning process is described in the above embodiment, it may be configured so that reconstruction conditions are set again for the projection data acquired in the scanning process and storing in a storage device such as a hard disk to generate an image.

<Fourth Embodiment>

Next, referring to FIGS. 20 and 21, the fourth embodiment will be described in detail. The fourth embodiment is an embodiment assuming electrocardiographic synchronous scanning that is generally performed for heart scanning and the like. In electrocardiographic synchronous scanning, the pulse of an object is measured by the electrocardiograph 7 etc. during scanning. Also, a spiral scan is performed while a multiple-scan overlap is being performed for a site to be scanned. Then, projection data of 180 degrees is calculated by combining with the projection data acquired in a certain cardiac phase section (a still phase) where a motion amount is the minimum to reconstruct an image.

In the fourth embodiment, a motion amount and a motion direction are considered to calculate a reconstruction data range in this electrocardiographic synchronous scanning.

Figure 20:
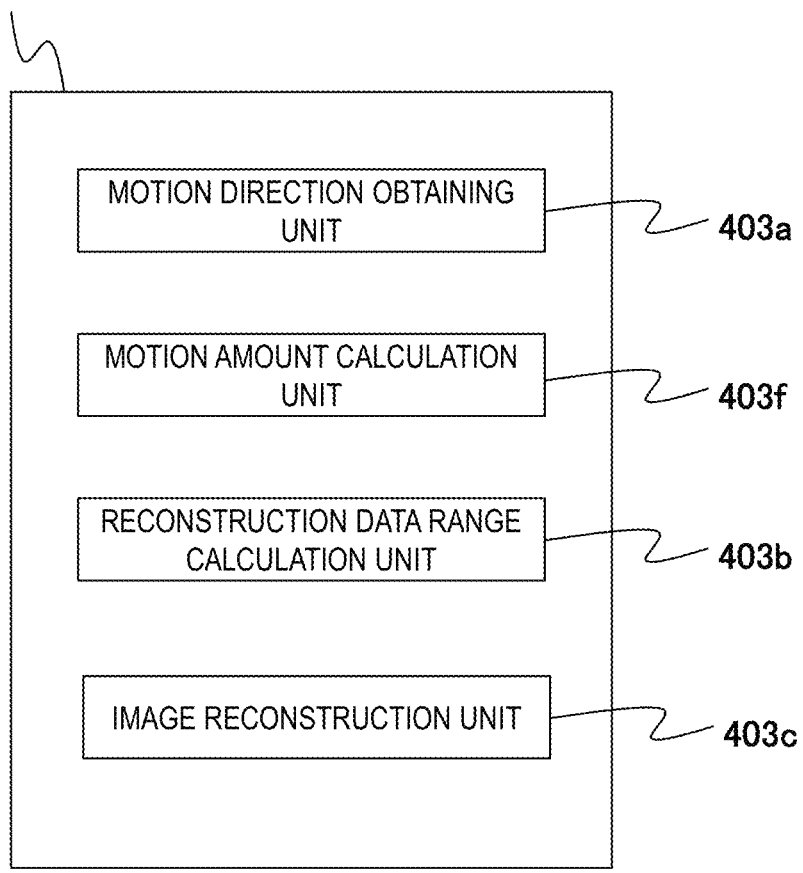
FIG. 20 is a functional block diagram of the image processing device 403 of the fourth embodiment.

FIG. 20 is a diagram showing the functional configuration of the image processing device 403 in the fourth embodiment. As shown in FIG. 20, the image processing device 403 of the fourth embodiment has the motion direction obtaining unit 403a, the motion amount calculation unit 403f, the reconstruction data range calculation unit 403b, and the image reconstruction unit 403c. That is, the fourth embodiment has the motion amount calculation unit 403f in addition to the functional configuration of the first embodiment shown in FIG. 2.

The motion amount calculation unit 403f calculates a motion amount of a site to be scanned. The motion amount, for example, can be calculated by comparing tomographic images whose phases are the same and scanning positions are different. Additionally, the calculation method of a motion amount is not limited to this, and the motion amount may be calculated by the other methods.

Figure 21:
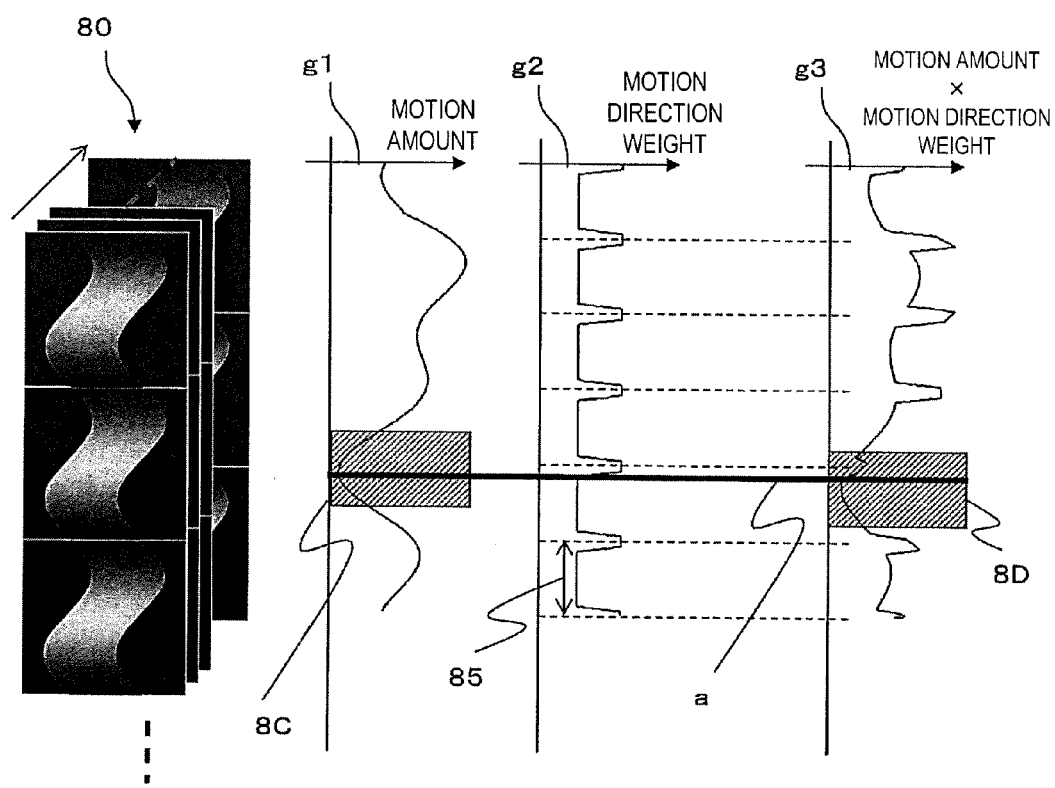
FIG. 21 is a diagram explaining a reconstruction data range in light of a motion amount and a motion direction.

The graph g1 of FIG. 21 is a graph showing the transition of the motion amount in each projection direction (X-ray irradiation angle). The vertical axis is a projection direction (an X-ray irradiation angle), and the horizontal axis is a motion amount. In the conventional image reconstruction process, the image processing device 403 reconstructs an image using projection data in the range 8C of at least 180 degrees by setting the projection data position a at which a motion amount is the minimum as the center.

In the present invention, the image processing device 403 calculates a reconstruction data range by considering a motion amount and a motion direction.

In the fourth embodiment, the reconstruction data range calculation unit 403b generates a motion-direction weight considering influence by a motion direction. Then, a reconstruction data range is adjusted by multiplying the motion direction weight by a motion amount. The graph g2 of FIG. 21 is a graph showing the transition of the motion-direction weight in the respective projection directions (X-ray irradiation angles). The vertical axis is a projection direction (an X-ray irradiation angle), and the horizontal axis is a motion-direction weight.

A motion-direction weight is a projection direction corresponding to a motion direction and is generated so that a value of "a motion amount×a motion-direction weight" becomes small.

The graph g3 of FIG. 21 is a graph showing the transition of a motion amount×a motion-direction weight in the respective projection directions (X-ray irradiation angles). The vertical axis is a projection direction (an X-ray irradiation angle), and the horizontal axis shows a value in which a motion amount was multiplied by a motion-direction weight.

As shown in the graph g3 of FIG. 21, the range 8D where a value of a motion amount×a motion-direction weight becomes the minimum is set as a reconstruction data range. The range 8D where a value of a motion amount×a motion-direction weight becomes the minimum may be set as an angle range of 180 degrees centering on a projection data position where a value of a motion amount×a motion-direction weight becomes the minimum or may be set as an angle range of 180 degrees where the total of values of motion amounts×motion-direction weights becomes the minimum.

Additionally, a motion direction may be set as a motion direction manually set by an operator as described in the first embodiment. Also, as described in the second embodiment, a motion direction may be determined by referring to the motion direction database 403d. Alternatively, as described in the third embodiment, a motion direction may be calculated by the image processing device 403 based on projection data etc.

When the reconstruction data range 8D considering a motion amount and a motion direction is calculated by the reconstruction data range calculation unit 403b, the image reconstruction unit 403c reconstructs an image using the projection data of the reconstruction data range 8D.

As described above, in the fourth embodiment, a motion amount and a motion direction of a target site are considered to calculate a reconstruction data range. Therefore, an image can be reconstructed using projection data with a small motion amount and small influence by a motion direction. Hence, motion artifacts can be further reduced.

<Fifth Embodiment>

Next, referring to FIGS. 22 to 23, the fifth embodiment will be described.

The first to fourth embodiments were described on the presumption that motion directions in all the positions in a scanning range were the same. However, the motion directions are not always the same in the entire scanning range. For example, there is a case where a different motion direction is shown depending on the slice position. Also, there is a case where a different motion direction is shown even in the same slice position depending on the site.

Therefore, in the fifth embodiment, a method to set a plurality of motion directions will be described.

Figure 22:
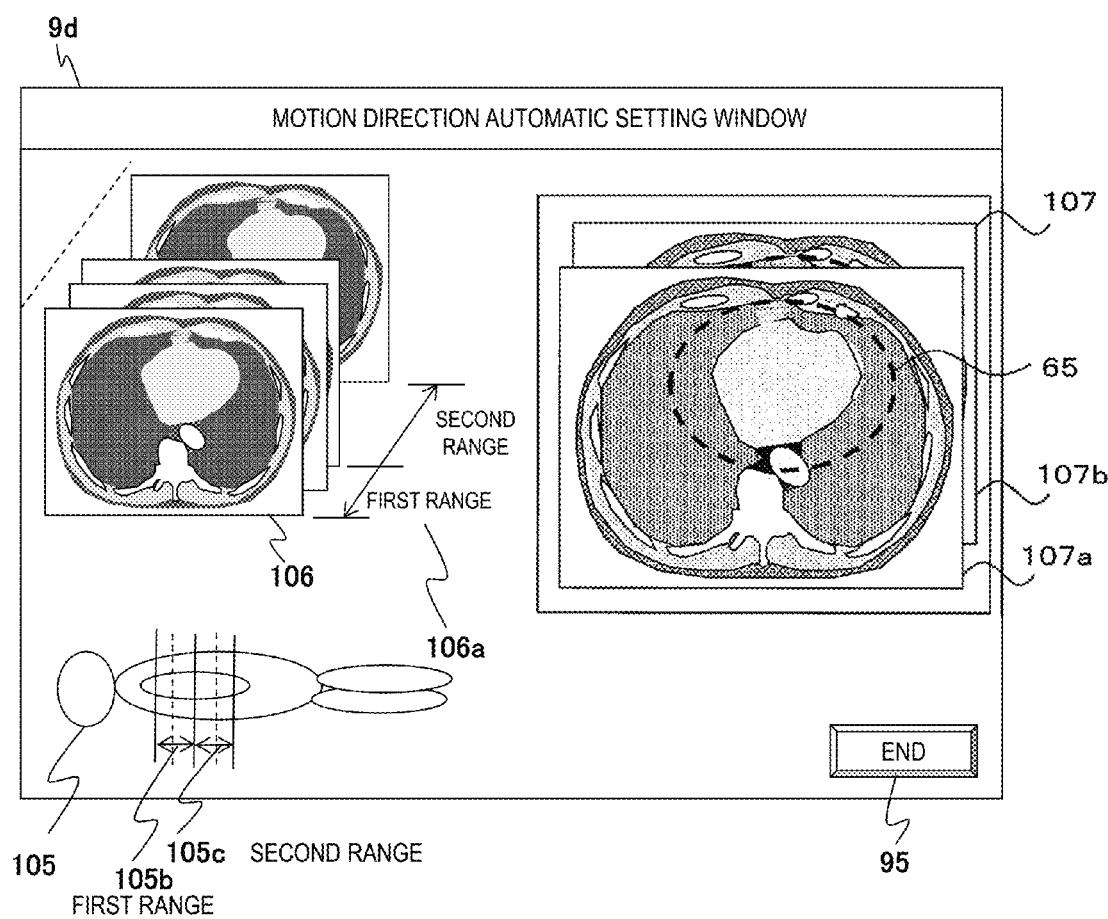
FIG. 22 is an example of the motion direction automatic setting window 9d (the fifth embodiment).

FIG. 22 is the motion direction automatic setting window 9d in case of automatically setting the respective motion directions in ranges different in the slice direction.

The motion direction automatic setting window 9d displays the object overall image 105, the serial images 106, and the tomographic images 107a and 107b. Then, the range setting GUIs 105b and 105c to set a slice direction range are displayed in the object overall image 105. A plurality of the range setting GUIs 105b and 105c can be displayed. Although two of the range setting GUIs 105b and 105c are provided in an example of FIG. 22, three or more of them may be provided. In the following description, a slice direction range to be set in the range setting GUI 105b is referred to as a first range. Also, a slice direction range to be set in the range setting GUI 105c is referred to as a second range. The lengths and positions of the arrows of the range setting GUIs 105b and 105c can be changed by operations with a mouse etc.

The GUI 106a displayed near the serial images shows image positions corresponding to the respective slice direction ranges set by the range setting GUIs 105b and 105c.

The tomographic images 107a and 107b are tomographic images in a representative slice position in a plurality of specified slice direction ranges. If the display window becomes narrow, it may be configured so that a tomographic image can be operated with it displayed in the forefront when any of the tomographic images is designated with a mouse etc. by partially overlapping the respective tomographic images 107a and 107b as shown in FIG. 22.

The image processing device 403 receives the settings for the target area 65 of a motion direction for the tomographic image 107 displayed in the forefront. Also, similarly to the third embodiment, a motion direction is calculated for each slice direction range.

Figure 23:
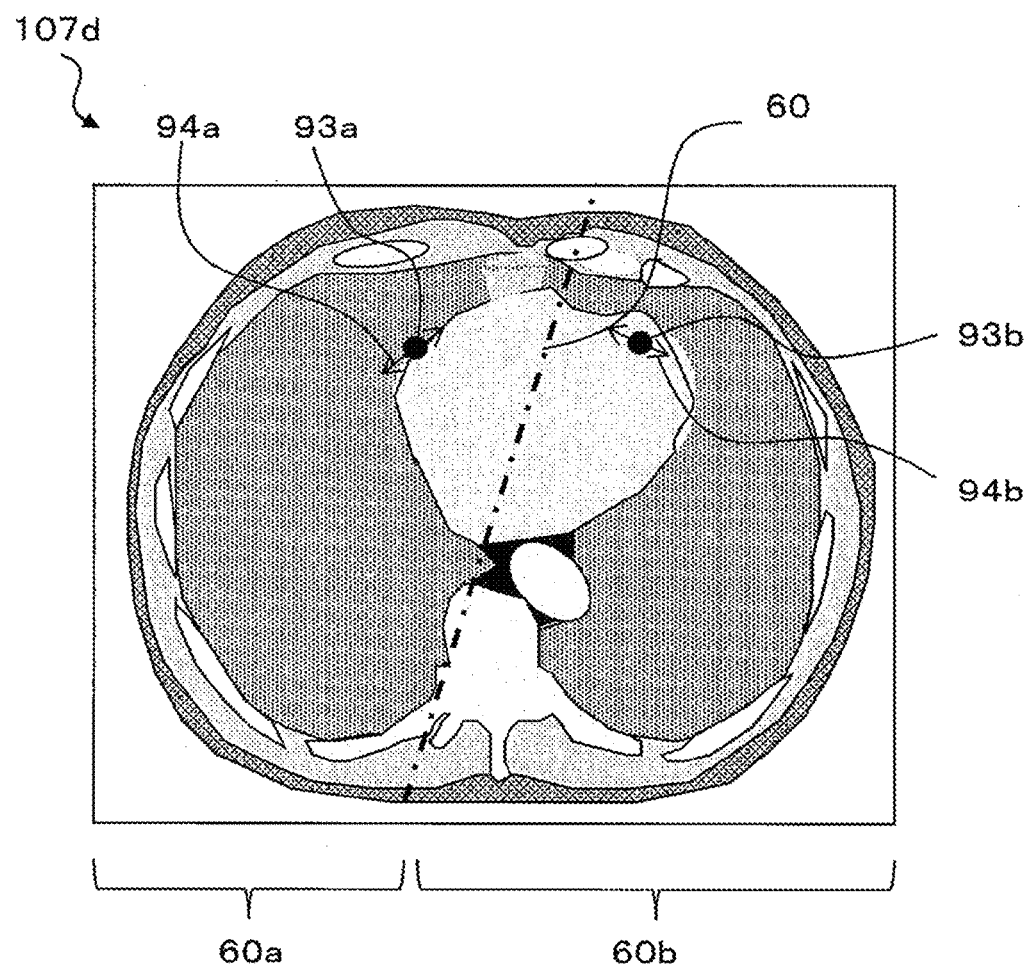
FIG. 23 is an example of manually setting a plurality of motion directions in an image.

Also, as shown in FIG. 23, a plurality of motion directions may be set in one image. In FIG. 23, the tomographic image 107d is divided into two regions by the dividing line 60. One region divided by the dividing line is referred to as the first region 60a, and the other region is referred to as the second region 60b. Additionally, the division number may not be limited to two, but also may be equal to or more than three.

In case of manually setting a motion direction, as shown in FIG. 23, the motion center marks 93a and 93b as well as the motion direction lines 94a and 94b are displayed in the respective regions. An operator changes positions of the motion center marks 93a and 93b as well as angles of the motion direction lines 94a and 94b. Hence, motion center points and motion directions can be set for the respective regions.

Also, a motion direction can be automatically set in the respective division regions 60a and 60b. In this case, the image processing device 403 has the motion detecting unit 403e as shown in the third embodiment. The motion detecting unit 403e calculates a motion direction in each division region based on projection data or an image. The image processing device 403 calculates a range of projection data (reconstruction data range) to be used for reconstructing an image based on a motion direction of each division region calculated by the motion detecting unit 403e. The reconstruction data range is set as a projection range of at least 180 degrees or more including a projection direction approximately corresponding to the motion direction similarly to the first to third embodiments. The image processing device 403 reconstructs an image using projection data in a reconstruction data range in each division region. Interpolation calculation is performed so that pixels on the boundary between image division regions are connected smoothly to generate an image.

As described above, the X-ray CT apparatus 1 of the fifth embodiment can set a plurality of motion directions in a scanning range and set a reconstruction data range according to each motion direction. Hence, an image can be generated using data in a reconstruction data range where motion influence becomes the minimum, for example, even in a case where a different motion direction is shown depending on the slice position and a case where a different motion direction is shown for each different site in the same slice position. This can reduce motion artifacts.

<Sixth Embodiment>

Next, referring to FIGS. 24 to 26, the sixth embodiment will be described in detail.

The sixth embodiment is an embodiment presuming a half scan. The half scan is a scanning method that acquires projection data by irradiating an X-ray only in a projection direction of a half rotation (a 180-degree range) and does not acquire projection data by stopping X-ray irradiation in a projection direction of the other half rotation.

Figure 24:
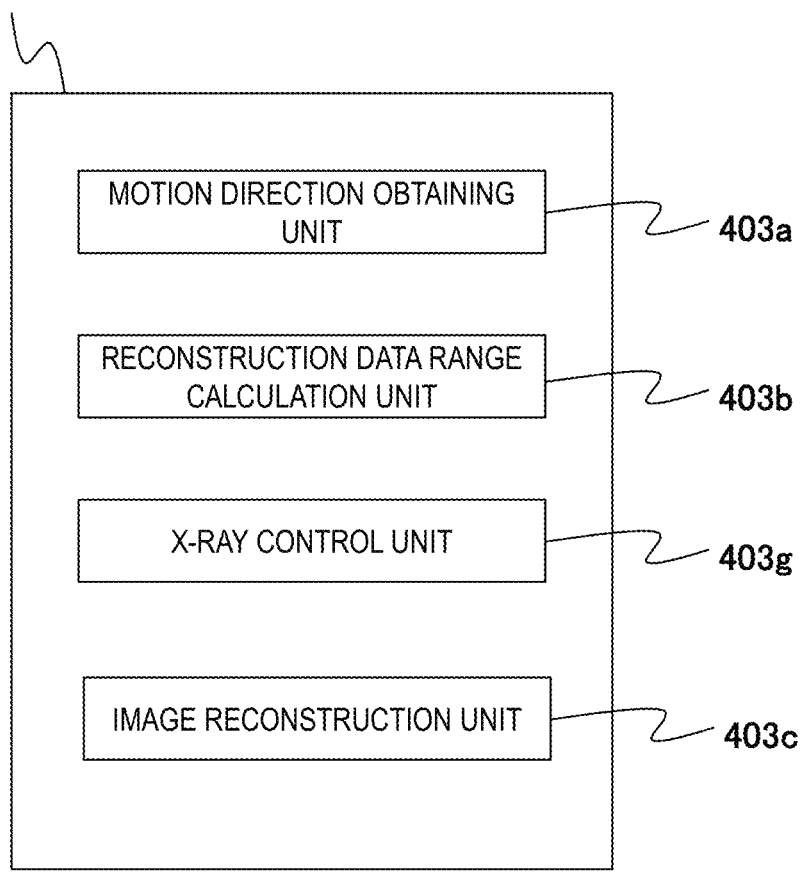
FIG. 24 is a functional block diagram of the image processing device 403 of the sixth embodiment.

FIG. 24 is a diagram showing the functional configuration of the image processing device 403 in the sixth embodiment.

As shown in FIG. 24, the image processing device 403 in the sixth embodiment has the motion direction obtaining unit 403a, the reconstruction data range calculation unit 403b, the X-ray control unit 403g, and the image reconstruction unit 403c.

That is, in the sixth embodiment, the X-ray control unit 403g is included in addition to the functional configuration of the first embodiment shown in FIG. 2.

The X-ray control unit 403g controls so that the X-ray tube 201 irradiates an X-ray at an X-ray irradiation angle equivalent to a reconstruction data range calculated by the reconstruction data range calculation unit 403b. Additionally, the X-ray control unit 403g controls not only an X-ray irradiation range but also an X-ray tube current, an X-ray tube voltage, etc. The X-ray tube current and the X-ray tube voltage are determined based on scanning conditions and reconstruction conditions.

Figure 25:
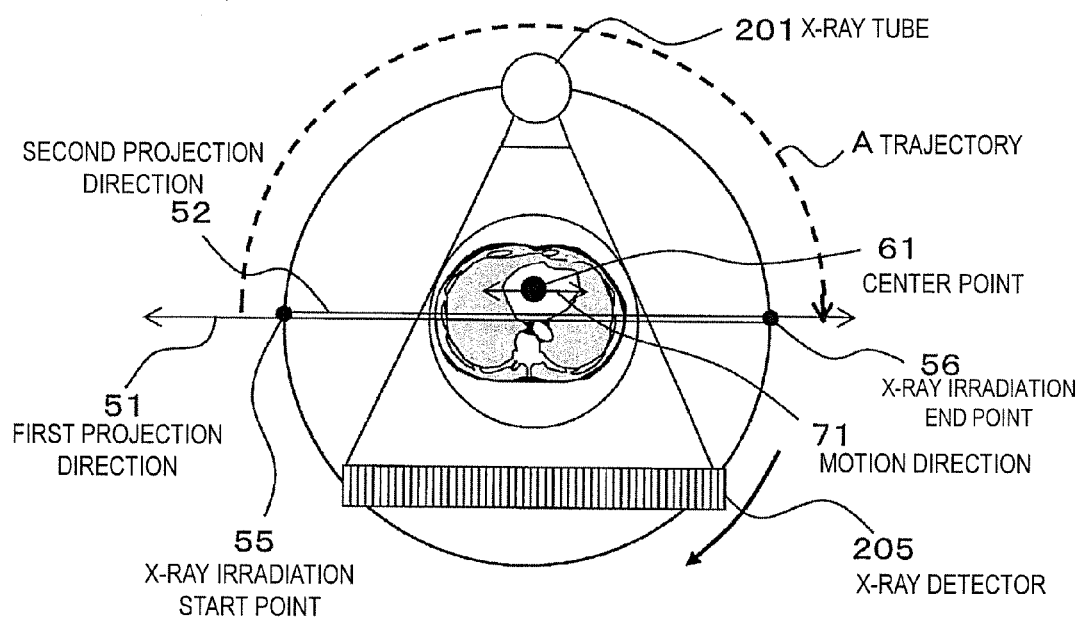
FIG. 25 is a diagram explaining an X-ray irradiation range in a half scan.

FIG. 25 shows a relationship between the motion direction 71 and the X-ray irradiation start point 55 as well as the X-ray irradiation end point 56 that correspond to a reconstruction data range (the trajectory A).

The image processing device 403 obtains a motion direction of a site to be scanned and then calculates the reconstruction data range 8 according to the motion direction. The reconstruction data range 8 is a range of at least 180 degrees or more including a projection direction (an X-ray irradiation angle) approximately corresponding to the motion direction. The motion direction may be set manually by an operator similarly to any of the methods of the first to third embodiments, may be determined by referring to the motion direction database 403d, or may be determined based on differences of the opposite projection data and the images by the motion detecting unit 403e.

The image processing device 403 transmits the calculated reconstruction data range 8 to the X-ray control unit 403g. The X-ray control unit 403g controls an X-ray irradiation timing so that the ends of the trajectory A corresponding to the reconstruction data range 8 become the X-ray irradiation start point 55 and the X-ray irradiation end point 56 as shown in FIG. 25.

The image processing device 403 acquires projection data in the range of 180 degrees from the X-ray irradiation start point 55 to the X-ray irradiation end point 56 while the bed table 3 is still in a predetermined slice position. Next, by moving the bed table 3 by a set amount, the projection data is acquired in the range of 180 degrees from the X-ray irradiation start point 55 to the X-ray irradiation end point 56. Alternatively, the projection data is acquired in the range of 180 degrees from the X-ray irradiation start point 55 to the X-ray irradiation end point 56 intermittently without moving the bed table 3 in the same position. By repeating such operations, projection data shown in FIG. 26 is acquired.

Figure 26:
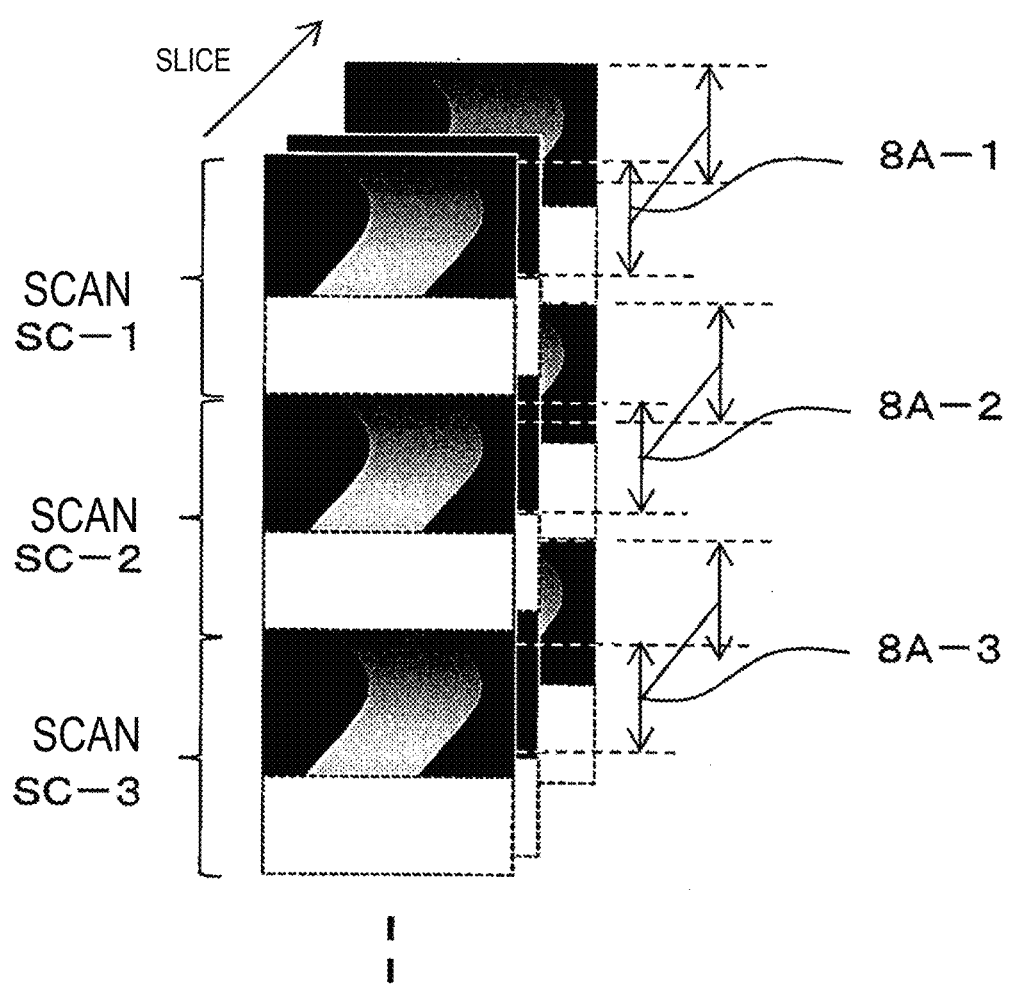
FIG. 26 is a diagram showing projection data and the reconstruction data ranges 8A-1, 8A-2, . . . acquired in case of FIG. 25.

FIG. 26 shows projection data acquired when a range equivalent to the reconstruction data range 8 is set as an X-ray irradiation region.

As shown in FIG. 26, the projection data of the scan SC-1 in the first rotation, SC-2 in the second rotation, SC-3 in the third rotation, . . . is acquired in each slice position. According to the projection data, an X-ray is irradiated to each of the scans SC-1, SC-2, and SC-3 in a range of the trajectory A. That is, the projection data is measured in ranges corresponding to the reconstruction data ranges 8A-1, 8A-2, and 8A-3, and the other range is in a state where there is no data.

The image processing device 403 reconstructs an image using data in the reconstruction data ranges 8A-1, 8A-2, and 8A-3.

As described above, the X-ray CT apparatus 1 of the sixth embodiment controls an X-ray irradiation range in association with the reconstruction data range 8 determined based on a motion direction. Therefore, a half scan can be performed at an optimal X-ray irradiation angle with low motion influence. Therefore, while motion artifacts are reduced, an exposure dose can also be reduced.

Additionally, X-ray irradiation control described in the sixth embodiment may be applied to, for example, a prospective ECG scan to be performed in heart scanning and the like. The prospective ECG scan is a scanning method to control an X-ray irradiation amount based on electrocardiac information measured by an electrocardiograph when a site to be scanned with a motion such as the heart is scanned. For example, an X-ray irradiation amount is increased in a phase where a motion amount of a site to be scanned becomes the minimum (static phase) and is reduced to the minimum required for reconstructing an image in the other phase.

For example, in the fourth embodiment, a motion amount is calculated at each projection angle (phase) as shown in the graph g3 of FIG. 21, and the reconstruction data range 8D is further determined by considering the motion amount. Thus, it is controlled so that an X-ray is irradiated at a projection angle corresponding to the determined reconstruction data range 8D and the X-ray irradiation stops at the other projection angle.

Hence, the present invention can be applied even in a prospective ECG scan. Therefore, while an exposure dose is reduced, motion artifacts can be reduced.

As described above, the X-ray CT apparatus 1 of the present invention determines a range of projection data to be used for image reconstruction (reconstruction data range) based on a motion direction of a site to be scanned and generates an image using the data in the reconstruction data range. Hence, when scanning a site to be scanned including a periodic motion, an image with low motion influence can be generated.

Additionally, various operation windows, operation methods, and the like described in the above embodiments are an example, and the other operation windows, operation methods, and the like may be used. In addition to this, it is apparent that those skilled in the art can consider various changes or modifications within the technical ideas disclosed in the present application, and it is understood that these naturally belong to the technical scope of the present invention.

DESCRIPTION OF REFERENCE NUMERALS

1: X-ray CT apparatus, 2: scanner gantry, 201: X-ray tube, 202: measurement controller, 205: X-ray detector, 210: rotary driving device, 3: bed table, 4: operation console, 401: system controller, 403: image processing device, 403a: motion direction obtaining unit, 403b: reconstruction data range calculation unit, 403c: image reconstruction unit, 403d: motion direction database, 403e: motion detecting unit, 403f: motion amount calculation unit, 403g: X-ray control unit 405: display device, 406: input device, 6: object, 7: electrocardiograph, 8 and 8A to 8D: reconstruction data range, A and B: trajectory of the X-ray tube 201, 51 first projection direction (X-ray irradiation angle), 52: second projection direction (X-ray irradiation angle), 55: X-ray irradiation start point, 56: X-ray irradiation end point, 61: center point, 71: motion direction, 9: condition setting window, 9a: motion direction manual setting window, 9c and 9d: motion direction automatic setting window, 84A to 84F: analysis image, g1: graph showing a motion amount of a site to be scanned at each projection angle, g2: graph showing a motion-direction weight, g3: graph showing a value of a motion amount×a motion-direction weight.

The invention claimed is:

1. An X-ray CT apparatus comprising:
an X-ray source for irradiating an X-ray to an object from the surroundings;
an X-ray detector for detecting an X-ray transmitted through the object;
an image processing device for generating projection data from the detected information about the transmitted X-ray and reconstructing a tomographic image of the object based on the projection data; and
a display device for displaying the tomographic image,
wherein the image processing device comprises:
a motion direction obtaining unit for obtaining a motion direction of a site to be scanned;
a reconstruction data range calculation unit for calculating a reconstruction data range that is a range of projection data to be used for reconstruction based on the motion direction; and
an image reconstruction unit for reconstructing an image using the projection data of the calculated reconstruction data range.

2. The X-ray CT apparatus according to claim 1, wherein the reconstruction data range calculation unit sets projection data in a projection range of at least 180 degrees or more including a projection direction approximately corresponding to a motion direction of the site to be scanned, as the reconstruction data range.

3. The X-ray CT apparatus according to claim 2, wherein the reconstruction data range calculation unit sets projection data in a projection range in which a distance between the site to be scanned and the X-ray source is closer from among the projection data in a projection range of at least 180 degrees or more including a projection direction same as a motion direction of the site to be scanned, as the reconstruction data range.

4. The X-ray CT apparatus according to claim 1, further comprising:
an input unit for inputting the motion direction,
wherein the motion direction obtaining unit obtains the motion direction input by the input unit.

5. The X-ray CT apparatus according to claim 4, wherein an angle of a line showing the motion direction input to the input unit, and
the motion direction obtaining unit obtains the line angle as the motion direction.

6. The X-ray CT apparatus according to claim 5, wherein a position of a motion center is further input to the input unit.

7. The X-ray CT apparatus according to claim 1, further comprising:
a storage unit for storing a motion direction according to the site to be scanned and a posture of the object,
wherein the motion direction obtaining unit obtains the motion direction according to the site to be scanned and the posture of the object that are set as scanning conditions, from the storage unit.

8. The X-ray CT apparatus according to claim 1, further comprising:
a motion detecting unit for detecting motion information of the site to be scanned,
wherein the motion direction obtaining unit obtains a motion direction of the site to be scanned from the motion information detected by the motion detecting unit.

9. The X-ray CT apparatus according to claim 8, wherein the motion detecting unit calculates motion information of the site to be scanned based on each of opposite projection data.

10. The X-ray CT apparatus according to claim 8,
wherein the motion detecting unit calculates motion information of the site to be scanned based on opposite images reconstructed respectively using projection data in opposite ranges.

11. The X-ray CT apparatus according to claim 8, further comprising:
a detection target area designating unit for designating a motion detection target area,
wherein the motion detecting unit detects the motion information in the motion detection target area.

12. The X-ray CT apparatus according to claim 1, further comprising:
a motion amount calculation unit for calculating a motion amount of the site to be scanned,
wherein the reconstruction data range calculation unit calculates the reconstruction data range based on the motion amount calculated by the motion amount calculation unit and the motion direction.

13. The X-ray CT apparatus according to claim 1,
wherein the reconstruction data range calculation unit calculates the reconstruction data range for each position of images to be generated.

14. The X-ray CT apparatus according to claim 1,
wherein an X-ray control unit is further included for controlling so that the X-ray source irradiates an X-ray at an X-ray irradiation angle equivalent to a reconstruction data range calculated by the reconstruction data range calculation unit.

15. The X-ray CT apparatus according to claim 1, further comprising:
a motion amount calculation unit for calculating a motion amount of the site to be scanned, and
an X-ray control unit for controlling so that the X-ray source irradiates an X-ray at an X-ray irradiation angle equivalent to the reconstruction data range calculated by the reconstruction data range calculation unit based on the motion amount calculated by the motion amount calculation unit and the motion direction.

16. An image reconstruction method including:
a projection data generation step of generating projection data in which the inside of an object was scanned;
a motion direction obtaining step of obtaining a motion direction of a site to be scanned;
a reconstruction data range calculation step of calculating a reconstruction data range that is a range of projection data to be used for reconstruction based on the motion direction; and
an image reconstruction step of reconstructing an image using projection data in the calculated reconstruction data range.

\* \* \* \* \*